United States Patent
Xu

(10) Patent No.: US 10,869,931 B2
(45) Date of Patent: Dec. 22, 2020

(54) POLYETHYLENE GLYCOL-MODIFIED ANGIOGENESIS INHIBITOR HM-1 AND APPLICATION THEREOF

(71) Applicant: NANJING ANJI BIOLOGICAL TECHNOLOGY CO.,LTD, Nanjing (CN)

(72) Inventor: Hanmei Xu, Nanjing (CN)

(73) Assignee: NANJING ANJI BIOLOGICAL TECHNOLOGY CO., LTD, Nanjing (CN)

( * ) Notice: Subject to any disclaimer, the term of this patent is extended or adjusted under 35 U.S.C. 154(b) by 0 days.

(21) Appl. No.: 16/090,251

(22) PCT Filed: Mar. 7, 2017

(86) PCT No.: PCT/CN2017/075864
§ 371 (c)(1),
(2) Date: Sep. 30, 2018

(87) PCT Pub. No.: WO2017/173905
PCT Pub. Date: Oct. 12, 2017

(65) Prior Publication Data
US 2019/0111144 A1    Apr. 18, 2019

(30) Foreign Application Priority Data

Apr. 6, 2016 (CN) .......................... 2016 1 0211000

(51) Int. Cl.
| | | |
|---|---|---|
| *A61K 38/10* | (2006.01) | |
| *A61K 47/60* | (2017.01) | |
| *C07K 7/08* | (2006.01) | |
| *A61P 19/02* | (2006.01) | |
| *A61P 27/02* | (2006.01) | |
| *A61P 35/00* | (2006.01) | |
| *A61P 29/00* | (2006.01) | |
| *A61K 9/00* | (2006.01) | |

(52) U.S. Cl.
CPC ............ *A61K 47/60* (2017.08); *A61K 9/0019* (2013.01); *A61K 38/10* (2013.01); *A61P 19/02* (2018.01); *A61P 27/02* (2018.01); *A61P 29/00* (2018.01); *A61P 35/00* (2018.01); *C07K 7/08* (2013.01)

(58) Field of Classification Search
CPC ...... A61K 38/10; A61K 47/60; A61K 9/0019; A61P 19/02; A61P 27/02; A61P 29/00; A61P 35/00; C07K 7/08
USPC ....... 530/300, 327, 326; 514/1.1, 19.3, 21.5, 514/21.4
See application file for complete search history.

(56) References Cited

FOREIGN PATENT DOCUMENTS

| CN | 1102417540 A | 4/2012 |
|---|---|---|
| CN | 102698270 A | 10/2012 |
| CN | 103623394 A | 3/2014 |
| CN | 1104045718 B | 9/2014 |
| CN | 105646667 A | 6/2016 |

OTHER PUBLICATIONS

CN104045718 machine translation, pp. 1-32. 2014.*
Zhai et al., "Enhanced circulation half-life of site-specific PEGylated rhG-CSF: Optimization of PEG molecular weight," Journal of Biotechnology, 142: 259-266. (Year: 2009).*
Zhou, Kang et al., "Studies of polyethylene glycol modification of HM-3 polypeptides", International Symposium on Pharmacogenomics and Drug Metabolism Enzyme and Gene Regulation & Journal of Nanjing University (Natural Science), vol. 46, May 31, 2010 (May 31, 2010), pp. 127-132, see abstract.
Wang, Bei et al., "Studies on the Pegylation Conditions of Polypeptide CPU-HM and Pharmacodynamics of Modified Products In Vivo", Chinese Journal of Pharmaceutical Biotechnology, vol. 23, No. 4, Dec. 31, 2016 (Dec. 31, 2016), ISSN: 1005-8915, pp. 313-317, see p. 313, right-hand column to p. 317.
Liu, Zhendong et al., "In Vivo Anti-Tumor Activity of Polypeptide HM-3 Modified by Different Polyethylene Glycols (PEG)", International Journal of Molecular Sciences, vol. 12, No. 4, Apr. 19, 2017 (Apr. 19, 2017), ISSN: 1422-0067, pp. 2650-2663, see abstract.

* cited by examiner

*Primary Examiner* — Julie Ha
(74) *Attorney, Agent, or Firm* — Zhihua Han; Wen IP LLC

(57) ABSTRACT

A polyethylene glycol-modified angiogenesis inhibitor HM-1 and its application are disclosed. The polypeptide sequence is mPEG-Arg-Gly-Ala-Asp-Arg-Ala-Gly-Gly-Gly-Gly-Arg-Gly-Asp (SEQ ID NO: 1), and mPEG . . . is chosen from mPEG-SC, mPEG2-NHS, mPEG-ALD or mPEG-bALD, with a molecular weight range of 500~40000. The polypeptide has been modified by polyethylene glycol, has the capacity to inhibit vascular endothelial cell migration and integrin affinity and binding, and can be used for the prevention and treatment of tumors, various types of inflammation, and neovascular eye diseases. The polyethylene glycol-modified angiogenesis inhibitor disclosed by the present invention is prepared by a synthetic method.

6 Claims, No Drawings

Specification includes a Sequence Listing.

SEQUENCE LISTING

<160> NUMBER OF SEQ ID NOS: 3

<210> SEQ ID NO 1
<211> LENGTH: 13
<212> TYPE: PRT
<213> ORGANISM: Artificial Sequence
<220> FEATURE:
<223> OTHER INFORMATION: Synthetic

<400> SEQUENCE: 1

Arg Gly Ala Asp Arg Ala Gly Gly Gly Gly Arg Gly Asp
1               5                   10

<210> SEQ ID NO 2
<211> LENGTH: 7
<212> TYPE: PRT
<213> ORGANISM: Artificial sequence
<220> FEATURE:
<223> OTHER INFORMATION: synthetic

<400> SEQUENCE: 2

Gly Gly Gly Gly Arg Gly Asp
1               5

<210> SEQ ID NO 3
<211> LENGTH: 6
<212> TYPE: PRT
<213> ORGANISM: Artificial sequence
<220> FEATURE:
<223> OTHER INFORMATION: synthetic

<400> SEQUENCE: 3

Arg Gly Ala Asp Arg Ala
1               5

POLYETHYLENE GLYCOL-MODIFIED ANGIOGENESIS INHIBITOR HM-1 AND APPLICATION THEREOF

CROSS REFERENCE TO RELATED APPLICATION

This application is a national stage application of International application number PCT/CN2017/075864, filed Mar. 7, 2017, titled "POLYETHYLENE GLYCOL-MODIFIED ANGIOGENESIS INHIBITOR HM-1 AND APPLICATION THEREOF," which claims the priority benefit of Chinese Patent Application No. 201610211000.5, filed on Apr. 6, 2016, which is hereby incorporated by reference in its entirety.

TECHNICAL FIELD

The present invention relates in general to the field of polypeptide medicines, and in particular, to a polyethylene glycol-modified angiogenesis inhibitor HM-1 and application thereof.

BACKGROUND

Angiogenesis refers to the generation of new capillaries from pre-existing blood vessels in the form of sprouting or non-sprouting, by the proliferation and migration of vascular endothelial cells on the basis of existing capillaries and/or venules. Angiogenesis plays a very important role in the process of placental formation, embryo development and wound healing. In many diseases, such as tumors, various types of inflammation and eye diseases (such as Age-Related Macular Degeneration (AMD)), angiogenesis also plays a vital role.

Malignant tumors are the leading killer of human health. In recent years, the incidence and mortality rate of cancer in China have been increasing. Infinite growth, invasion, and metastasis are signs of cancer malignancy and the leading cause of treatment failure and death. Therefore, controlling tumor growth, invasion and metastasis is the main measure to improve prognosis and improve survival rate. In the 1970s, Folkman first proposed in the New England Journal of Medicine that tumor growth depends on neovascularization. Tumor angiogenesis is the morphological basis of tumor growth and metastasis. It not only provides nutrition and oxygen to tumors, but also exports a large number of tumor cells to the host resulting in tumor growth and metastasis. Most malignant solid tumors such as ovarian cancer, liver cancer, cervical cancer, and breast cancer are vascular-dependent tumors. Therefore, inhibition of tumor angiogenesis is an important anti-cancer measure.

Arthritis inflammatory diseases are one of the most common diseases that endanger human health. They are inflammatory diseases that occur in human joints and surrounding tissues. The number of people suffering from such diseases in China is increasing year by year. Such diseases mainly include rheumatoid arthritis, gouty arthritis, reactive arthritis, osteoarthritis, psoriatic arthritis, infectious arthritis, traumatic arthritis and ankylosing spondylitis. Rheumatoid arthritis (RA) is a chronic progressive arthritis whose cause has not yet been affirmed. It is generally considered to be an autoimmune disorder and is the result of fratricidal destruction of the body's defense system. Genetics, infection, cold and humidity, etc. may all be pathogenic factors. In the pathological process of RA, angiogenesis is a landmark histological change. Neovascularization is accompanied by synovial hyperplasia and inflammatory cell infiltration, which is the basis of vasospasm formation and joint destruction in RA. Therefore, inhibiting the formation of new blood vessels is the key to the treatment of such diseases. Inhibiting angiogenesis not only prevents the delivery of oxygen and nutrients to the synovial membrane, but also directly leads to the degeneration of blood vessels, thereby inhibiting the synovial growth of RA.

The pathogenesis of ophthalmological diseases, such as Iris neovascular eye disease, choroidal neovascular eye disease, retinal neovascular eye disease, and corneal neovascular eye disease, is related to the excessive formation of new blood vessels. Lacking normal physiological structure of mature blood vessels, new blood vessels have high permeability, are easy to rupture, as a result blood flows into the vitreous cavity, causing bleeding in the fundus, leading to blurred vision or completely lost vision in patients, which seriously affects the quality of life of the patients. Therefore, inhibition of angiogenesis is the key to the treatment of these diseases, and proliferation and migration of endothelial cells is a key step in the formation of new blood vessels.

Endostatin (ES) is the carboxy-terminal non-collagen region fragment of macromolecular collagen XVIII composed of 183 amino acid residues with a relative molecular mass of 20 kD. Endostatin is an angiogenesis inhibitor that impedes the nutrients supply to tumors by inhibiting tumor neovascularization. Since it can specifically act on endothelial cells and does not have a significant effect on blood vessels in normal tissues, it has no toxic effect or side effects and does not produce drug resistance. Endostatin has shown certain anti-tumor effect in animal models in vivo, no significant anti-tumor effect in clinical trials. A drug application based on endostatin was finally rejected by the US Food and Drug Administration (FDA). Related literature reports that the peptide consisting of the 6th to 49th amino acids (aa) and 134th to 178th amino acids of endostatin can inhibit the proliferation and migration of human umbilical vein endothelial cells, and the activity is even higher than that of endostatin itself. Therefore, truncating endostatin and identifying potential active fragment(s) would not only reveal the mechanism of the macromolecule, but also reduce the cost of drug development and provide insights for the development of peptide-based treatment for these illnesses.

Integrin is a family of receptors that recognize a variety of extracellular matrix components. It is widely distributed on the cell surface and mediates cell-to-extracellular matrix and cell-to-cell adhesion. It also mediates angiogenesis by connecting intracellular cytoskeletal proteins with extracellular matrix molecules. These receptors are composed of two chains of α and β. Currently, 15 α chains and 9 β chains have been found. The combination of different α chains and β chains determines the specificity of the ligands, integrin α1β1, α2β1, α3β1, α6β1, α6β4, α5β1, αvβ3, and αvβ5 are involved in angiogenesis and cell migration, and αvβ3 may affect several key processes in carcinogenesis. αvβ3 can be expressed in a variety of cell types, recognizes the Arg-Gly-Asp (RGD) in the ligand molecule, and is involved in tumor angiogenesis, invasion, metastasis, inflammation, wound healing and coagulation physiology and pathology. Therefore, the RGD sequence can be used as a carrier to target transport to neovascular endothelial cells, thereby achieving a more efficient treatment for neovascular diseases. Patent application ZL201410324568.9 titled "multifunctional fusion polypeptide, preparation method and application thereof", introduced several angiogenesis inhibitor polypeptides, one of which is HM-1, and the sequence is: Arg-Gly-Ala-Asp-Arg-Ala-Gly-Gly-Gly-Gly-Arg-Gly-Asp (SEQ ID NO: 1). This sequence contains the integrin ligand sequence (Gly-Gly-Gly-Gly-Arg-Gly-Asp) (SEQ ID NO: 2) and the neovascularization inhibition sequence (Arg-Gly-Ala-Asp-Arg-Ala) (SEQ ID NO: 3). This polypeptide has been proved to have a good anti-tumor effect by repeated in vitro and in vivo activity evaluation, and can significantly inhibit endothelial cell migration, inhibit tumor angiogenesis, and thereby inhibit tumor growth. However, the above polypeptides have a short half-life and need to be administered frequently, which brings pain and inconvenience to the patient.

In the literature report, the modification or alteration of the molecular structure is a common method to solve the problem of short half-life and continuous drug administration. Among them, chemical modification is the most widely used. The commonly used chemical modifier is polyethylene glycol (PEG), dextran, polyamino acid, polyanhydride, and the like. PEG is non-toxic, non-immunogenic, and water-soluble. It is recognized by the FDA as an auxiliary material and modifier for pharmaceuticals. After modification by PEG, protein- or peptide-based drugs increase in molecular weight and decrease in glomerular filtration rate. The barrier function of PEG also protects proteins and peptides from hydrolysis by proteolytic enzymes and reduces the production of neutralizing antibodies. These changes ameliorate the shortcomings of protein- or peptide-based drugs such as in rapid removal from body, high immunogenicity, short duration of effective blood drug concentration, and frequent administration. A variety of PEG-modified protein drugs have been marketed. However, success of PEG modification is uncertain, unpredictable, and far from routine, since PEG usually negatively affects the biological activity of proteins and peptides. The magnitude of the effects is related to the modifier, the modification conditions and the nature of the protein or the peptide itself. The biological activity of the modified product can be determined by in vitro and in vivo pharmacodynamic tests.

Angiogenesis inhibitors are a class of drugs that have received strong attention in the treatment of neovascular diseases in recent years. Among these angiogenesis inhibitors, angiostatin and endostatin are the most prominent. Although these vascular inhibitors have very attractive prospects, their defects are also very obvious: the targets of angiogenesis inhibitors have not been clear so far, and the specificity and selectivity of blood vessels are not good enough, and the effect is limited, resulting in large dosing. Therefore, a good anti-angiogenic drug should be specific for molecular markers of neovascularization to achieve a targeting effect to neovascularization, and to increase the inhibitory effect of the drug on angiogenesis as a whole. It is imperative to achieve efficient inhibition of angiogenesis with only low-dose of drugs can. So far, there is report that Avastin has been successfully used in the treatment of ocular diseases, and there is still no such drug developed in China. Inhibition of angiogenesis by the integrin target of the present invention would be a new option for the treatment of such ocular diseases.

SUMMARY

Problems to Solve

In view of the shortcomings of the existing angiogenesis inhibitor polypeptide HM-1, such as short half-life, high plasma clearance rate, frequent administration, etc., the present invention provides a polyethylene glycol-modified angiogenesis inhibitor HM-1 and application thereof. HM-1 was modified by PEG, but during the modification of PEG, the reaction conditions would inevitably affect the yield of the modified product, the type of the product and the stability of PEG. The type and molecular weight of PEG also have a certain degree of influence on the biological activity of the modified product. In addition, when the types of PEG are different, the reaction conditions may produce by-products, which affect the purity of the modified product and cause certain difficulties for isolation and purification. Therefore, PEG with different molecular weights and different reaction conditions for modifying HM-1 were explored, and a single-modification product was unexpectedly found that is stable, high yield, and efficacious. The modified products were subjected to various in vitro and in vivo test for drug efficacy. More modified products that have prolonged half-life in vivo and retain high level biological activity are identified for future use in prevention and treatment of tumors, various types of inflammation, and neovascular eye diseases.

However, the modified products in a solution state have poor stability and tend to lose activity during production process. In order to improve their stability, the modified product solution is subjected to rotary evaporation concentration, vacuum freeze-dried, and stored at −70° C.; since the modified products in the solution state have poor stability, they are sensitive to high temperature, and the temperature during rotary evaporation can be high. The excessive time spent during the rotary evaporation may accelerate the degradation of the modified product; if the temperature is rendered too low during the concentrating process, the concentrating process can be unduly prolonged which may also negatively affect the stability of the products. Therefore, we also explored the temperature and time of rotary evaporation to establish conditions wherein the concentrating process can be finished as quickly as possible without affecting product stability.

Technical Solutions

In order to solve the above problems, the technical solution adopted by the present invention is as follows:

A polyethylene glycol-modified angiogenesis inhibitor HM-1 having the sequence of mPEG-Arg-Gly-Ala-Asp-Arg-Ala-Gly-Gly-Gly-Gly-Arg-Gly-Asp (SEQ ID NO: 1).

Preferably, the mPEG is mPEG-SC (monomethoxy polyethylene glycol-succinimide carbonate), $mPEG_2$-NHS (branched monomethoxy polyethylene glycol-succinimidyl ester), mPEG-ALD (monomethoxy polyethylene glycol-propionaldehyde) or mPEG-bALD (monomethoxy polyethylene glycol-butyraldehyde), wherein the molecular weight ranging PEG is from 500 to 40,000 Daltons.

Preferably, the sequences are:

(SEQ ID NO: 1)
mPEG-$SC_{5k}$-Arg-Gly-Ala-Asp-Arg-Ala-Gly-Gly-Gly-Gly-Arg-Gly-Asp;

(SEQ ID NO: 1)
mPEG-$SC_{10k}$-Arg-Gly-Ala-Asp-Arg-Ala-Gly-Gly-Gly-Gly-Arg-Gly-Asp;

(SEQ ID NO: 1)
mPEG-$SC_{20k}$-Arg-Gly-Ala-Asp-Arg-Ala-Gly-Gly-Gly-Gly-Arg-Gly-Asp;

(SEQ ID NO: 1)
mPEG-$SC_{40k}$-Arg-Gly-Ala-Asp-Arg-Ala-Gly-Gly-Gly-Gly-Arg-Gly-Asp;

-continued mPEG$_2$-NHS$_{5k}$-Arg-Gly-Ala-Asp-Arg-Ala-Gly-Gly-Gly-Gly-Arg-Gly-Asp;  (SEQ ID NO: 1)

mPEG$_2$-NHS$_{10k}$-Arg-Gly-Ala-Asp-Arg-Ala-Gly-Gly-Gly-Gly-Arg-Gly-Asp;  (SEQ ID NO: 1)

mPEG$_2$-NHS$_{20k}$-Arg-Gly-Ala-Asp-Arg-Ala-Gly-Gly-Gly-Gly-Arg-Gly-Asp;  (SEQ ID NO: 1)

mPEG$_2$-NHS$_{40k}$-Arg-Gly-Ala-Asp-Arg-Ala-Gly-Gly-Gly-Gly-Arg-Gly-Asp;  (SEQ ID NO: 1)

mPEG-ALD$_{5k}$-Arg-Gly-Ala-Asp-Arg-Ala-Gly-Gly-Gly-Gly-Arg-Gly-Asp;  (SEQ ID NO: 1)

mPEG-ALD$_{10k}$-Arg-Gly-Ala-Asp-Arg-Ala-Gly-Gly-Gly-Gly-Arg-Gly-Asp;  (SEQ ID NO: 1)

mPEG-ALD$_{20k}$-Arg-Gly-Ala-Asp-Arg-Ala-Gly-Gly-Gly-Gly-Arg-Gly-Asp;  (SEQ ID NO: 1)

mPEG-ALD$_{40k}$-Arg-Gly-Ala-Asp-Arg-Ala-Gly-Gly-Gly-Gly-Arg-Gly-Asp;  (SEQ ID NO: 1)

mPEG-bALD$_{5k}$-Arg-Gly-Ala-Asp-Arg-Ala-Gly-Gly-Gly-Gly-Arg-Gly-Asp;  (SEQ ID NO: 1)

mPEG-bALD$_{10k}$-Arg-Gly-Ala-Asp-Arg-Ala-Gly-Gly-Gly-Gly-Arg-Gly-Asp;  (SEQ ID NO: 1)

mPEG-bALD$_{20k}$-Arg-Gly-Ala-Asp-Arg-Ala-Gly-Gly-Gly-Gly-Arg-Gly-Asp;  (SEQ ID NO: 1)
or mPEG-bALD$_{40k}$-Arg-Gly-Ala-Asp-Arg-Ala-Gly-Gly-Gly-Gly-Arg-Gly-Asp.  (SEQ ID NO: 1)

A medicament, medicine, or drug made from, or an application of, the above described polyethylene glycol-modified angiogenesis inhibitor HM-1, for treating tumors, inflammation, and neovascular eye diseases.

Preferably, the tumors comprise a primary or secondary cancer, melanoma, hemangiomas, and sarcomas originating from human head, neck, brain, thyroid, esophagus, pancreas, lung, liver, stomach, breast, kidney, gallbladder, colon or rectum, ovary, cervix, uterus, prostate, bladder, and testis.

Preferably, the inflammation comprises rheumatoid arthritis, gouty arthritis, reactive arthritis, osteoarthritis, psoriatic arthritis, infectious arthritis, traumatic arthritis, and ankylosing spondylitis.

Preferably, the neovascular eye diseases comprise iris neovascular eye disease, choroidal neovascular eye disease, retinal neovascular eye disease, and corneal neovascular eye disease.

A medicine for treating tumor, inflammation and neovascular eye diseases, wherein the drug contains the polyethylene glycol-modified angiogenesis inhibitor HM-1 described above, wherein administration of the medicine is by injection.

Preferably, the administration of the medicine includes subcutaneous injection, intramuscular injection, intravenous injection, intraocular vitreous injection, and intravenous drip.

The preparation method of the above polyethylene glycol-modified angiogenesis inhibitor HM-1, including the steps of: (1) synthesizing the peptide with the sequence of Arg-Gly-Ala-Asp-Arg-Ala-Gly-Gly-Gly-Gly-Arg-Gly-Asp (SEQ ID NO: 1); (2) modifying the peptide Arg-Gly-Ala-Asp-Arg-Ala-Gly-Gly-Gly-Gly-Arg-Gly-Asp with mPEG (SEQ ID NO: 1); (3) separating and purifying the modified products into pure polyethylene glycol-modified angiogenesis inhibitor HM-1 in solution state; (4) The modified product solution obtained by isolation and purification was subjected to rotary evaporation concentrating, followed by vacuum freeze-drying to obtain a modified product powder, which was stored at −70° C.

The specific process of mPEG modification of HM-1 is as follows: various conditions that may affect the modification reaction, including: reaction temperature, reaction time, molar ratio of mPEG to HM-1, type of buffer, pH of buffer, concentration of buffer (Table 2), the concentration of the polypeptide and the concentration of the reducing agent sodium cyanoborohydride ($N_aCNBH_3$) were initially explored and re-optimized, and the modification rate of the single modified product was analyzed by the area normalization method using high performance liquid chromatography. The analysis was carried out to screen out various reaction conditions in which the yield of various mPEG-modified HM-1 single-modification products was high. The specific chromatographic conditions are:

Analytical column: COSMOSIL, 250 mm×4.6 mm (5 μm resin);

Mobile phase: phase A is water (plus 0.1% TFA), phase B is acetonitrile (plus 0.1% TFA);

Loading amount: 20 μL;

Flow rate: 1 mL/min;

Detection wavelength: 220 nm;

Elution gradient: see Table 1

TABLE 1

Elution Gradient used for Detecting the Yield of Modified Products

| Time (min) | Flow Rate (mL/min) | A % | B % | Wavelength nm |
|---|---|---|---|---|
| 0 | 1 | 95 | 5 | 220 |
| 5 | 1 | 88 | 12 | 220 |
| 17 | 1 | 60 | 40 | 220 |
| 30 | 1 | 30 | 70 | 220 |

TABLE 2

Buffers for various mPEG

| Type of PEG | Type of Buffers | Buffer pH | Buffer Concentration (mol/L) |
|---|---|---|---|
| mPEG-SC | $Na_2HPO_4$—$NaH_2PO_4$ | 7.5~8.5 | 0.05 |
|  |  |  | 0.1 |
|  |  |  | 0.2 |
| mPEG$_2$-NHS | $H_3BO_3$—$Na_2B_4O_7$ | 8.0~9.0 | 0.05 |
|  |  |  | 0.1 |
|  |  |  | 0.2 |
| mPEG-ALDand | $Na_2HPO_4$—$NaH_2PO_4$ | 5.0~6.0 | 0.05 |
|  |  |  | 0.1 |
|  |  |  | 0.2 |
| mPEG-bALD | $CH_3COOH$—$NaCH_2COOH$ |  | 0.05 |
|  |  |  | 0.1 |
|  |  |  | 0.2 |

The initial exploring of the various PEG modification conditions was performed as follows: the reaction temperature was fixed at 4° C., the molar ratio of mPEG to HM-1 was set at 1.5:1, and the polypeptide concentration was set as 1 mg/mL, and the reaction buffer type and concentration are tested and selected: (1) screening of buffer concentration form PEG-SC modification of HM-1: reaction time was 6 hours, and $Na_2HPO_4$—$NaH_2PO_4$ with pH of 7.5, 8.0, 8.5 was prepared at concentrations of 0.05 mol/L, 0.1 mol/L and 0.2 mol/L, respectively. The modification reactions were performed under the various buffers concentration and the various buffer pH, and the modification rate of the single-modified product was detected. The results showed that the mPEG-SC with different molecular weights had the highest single-modification yield at the concentration of 0.1 mol/L and pH 8.5 in $Na_2HPO_4$—$NaH_2PO_4$ buffer, up to 90.0%, and the modification rate increased with the increase of pH. Therefore, 0.1 mol/L $Na_2HPO_4$—$NaH_2PO_4$ buffer was used to optimize the mPEG-SC modification conditions. (2) Screening buffer concentration for $mPEG_2$-NHS modification of HM-1: the concentration of reducing agent $NaCNBH_3$ was 0.05 mol/L, and the reaction time was 10 hours, and the $H_3BO_3$—$Na_2B_4O_7$ buffers were prepared at the concentrations of 0.05 mol/L, 0.1 mol/L and 0.2 mol/L, with pH of 8.0, 8.5, and 9.0. The modification reactions were carried out in buffers of different concentrations and different pH, and the modification rate of the single-modified products were measured. The results showed that the $mPEG_2$-NHS with different molecular weights had the highest single-modification yield in the $H_3BO_3$-$Na_2B_4O_7$ buffer with a concentration of 0.05 mol/L and pH 8.5, up to 58.8%, but by-products production increased with increasing pH. Therefore, 0.05 mol/L $H_3BO_3$-$Na_2B_4O_7$ buffer was used to optimize the $mPEG_2$-NHS modification conditions. (3) Screening of species and concentration of buffers used in mPEG-ALD and mPEG-bALD modification of HM-1: the reaction time was 10 h, and the $Na_2HPO_4$—$NaH_2PO_4$ buffer and $CH_3COOH$—$NaCH_2COOH$ buffer were prepared at the concentrations of 0.05 mol/L, 0.1 mol/L and 0.2 mol/L, with pH at the 5.0, 5.5, and 6.0, and the modification rate of single-modified products was measured at the different concentrations and different pH buffers. The results showed that the mPEG-ALD and mPEG-bALD with different molecular weights had the highest single-modification yield in the $CH_3COOH$—$NaCH_2COOH$ buffer at a concentration of 0.1 mol/L and pH 5.5, with the highest yields of 85.6% and 96.2%, respectively. As a result, further optimization of mPEG-ALD and mPEG-bALD modification conditions were performed using 0.1 mol/L $CH_3COOH$—$NaCH_2COOH$ buffer.

Further optimization of various PEG modification conditions was performed as follows: based on initial exploration results, under the selected buffer concentrations and buffer types for various PEG modification, other key factors were further optimized. (1) Optimization of conditions for mPEG-SC modification of HM-1: at the fixed condition of the reaction temperature of 4° C., a peptide concentration of 1 mg/mL, and 0.1 mol/L $Na_2HPO_4$—$NaH_2PO_4$ buffer, three factors of the molar ratio of mPEG to HM-1, the pH of the buffer, and the reaction time were subjected to a three-factor three-level orthogonal test (Table 3). The orthogonal test results were analyzed by the range analysis. The pH change of the buffer was the key factor affecting the reaction. The average modification rates at pH 7.5, 8.0, and 8.5 were 50.88%, 74.55%, and 81.68%, respectively. The effect is significant, and the pH of the buffer can be re-optimized. (2) Optimization of conditions for $mPEG_2$-NHS modification of HM-1: at a fixed reaction temperature of 4° C., a peptide concentration of 1 mg/mL, and 0.05 mol/L $H_3BO_3$-$Na_2B_4O_7$ buffer, three factors including molar ratio of mPEG to HM-1, the pH of the buffer, and the reaction time were subjected to a three-factor three-level orthogonal test (Table 4). The orthogonal test results were analyzed by the range analysis. The pH change of the buffer was the key factor affecting the reaction. The average modification rates at pH 8.0, 8.5, 9.0 were 37.40%, 50.72% and 25.63%, respectively. The effect is significant, and as the pH increases, the content of by-products increases, which is not conducive to the isolation and purification of the modified product, so the pH of the buffer can be re-optimized. (3) Optimization of conditions for mPEG-ALD and mPEG-bALD modification of HM-1: at the fixed reaction temperature of 4° C., peptide concentration of 1 mg/mL, and 0.05 mol/L $H_3BO_3$—$Na_2B_4O_7$ buffer, four factors including molar ratio pf mPEG and HM-1, the pH of the buffer, the reaction time, and the concentration of the reducing agent NaCNBH3 were analyzed in a four-factor, three-level orthogonal test (Table 5). The orthogonal test results were analyzed by the range analysis. The pH of the buffer was the key factor affecting the modification of HM-1 by mPEG-ALD. The average modification rates at pH 5.0, 5.5 and 6.0 were 66.40%, 75.00% and 85.32%, respectively. The effect on the modification rate was significant. The molar ratio of PEG to peptide was the key influence factor of mPEG-ALD modification of HM-1. The average modification rates at the molar ratio of 1.1:1, 1.3:1 and 1.5:1 are 86.18%, 87.63% and 95.23%, respectively. The effect on the modification rate was significant. In addition, since the reducing agent NaCNBH3 has certain cytotoxicity, its dosage should be reduced as much as possible. Therefore, the pH of the buffer and the concentration of NaCNBH3 can be re-optimized during mPEG-ALD modification of HM-1, the molar ratio of PEG to peptide and the NaCNBH3 concentration can be re-optimized during the mPEG-bALD modification of HM-1.

Re-optimization of various PEG modification conditions: the key factors of different PEG modification were re-optimized according to the optimization results of the modification conditions. (1) re-optimization of conditions for mPEG-SC modification of HM-1: under the condition of reaction temperature was 4° C., peptide concentration was 1 mg/mL, molar ratio of mPEG to HM-1 was 1.5:1, and reaction time was 3 hours, the pH of the buffer was re-optimized in 0.1 mol/L $Na_2HPO_4$—$NaH_2PO_4$ buffer at pH 8.2, 8.3, 8.4, 8.5, 8.6 and 8.7, respectively. The results showed that the yield of single modification increased with pH at pH 8.2-8.5. When the pH was higher than 8.5, reaction by-products were produced, and the yield of by-products increased with the increase of pH, which was not conducive to the isolation and purification of modified products. Therefore, the pH should be strictly controlled to 8.5. (2) Re-optimization of conditions for $mPEG_2$-NHS modification of HM-1. Under the condition of reaction temperature was 4° C., peptide concentration was 1 mg/mL, molar ratio of mPEG to HM-1 was 1.5:1, and reaction time was 10 h, the pH of the buffer was re-optimized in a 0.05 mol/L $H_3BO_3$—$Na_2B_4O_7$ buffer at pH 8.3, 8.4, 8.5, 8.6 and 8.7, respectively. The results showed that the yield of single modification increased with the increase of pH at pH 8.2-8.5. When the pH was higher than 8.5, the by-product yield increased with the increase of pH and showed a shoulder peak pattern with the target product, which was not conducive to isolation and purification of modified product, so the pH should be strictly controlled to 8.5. (3) Re-optimization of conditions for mPEG-ALD modification of HM-1: 1) re-optimization of buffer pH: under the conditions of reaction temperature was 4° C., peptide concentration was 1 mg/mL, molar ratio of mPEG to HM-1 was 1.5:1, $NaCNBH_3$ concentration was 0.05 mol/L, and reaction time was 10 hours, the pH of the buffer is re-optimized in 0.1 mol/L $CH_3COOH$—$NaCH_2COOH$ buffer with pH of 5.8, 5.9, 6.0, 6.1 and 6.2, respectively. The results showed that the yield of single modification increased slightly with the increase of pH at pH 5.8-6.0. When the pH was greater than 6.0, by-products appeared, which was not conducive to the isolation and purification of the modified product, so the pH was controlled to 5.8-6.0. 2) Re-optimization of $NaCNBH_3$ concentration: under the conditions of reaction temperature was 4° C., peptide concentration was 1 mg/mL, molar ratio of mPEG to HM-1 was 1.5:1, pH of $CH_3COOH$—$NaCH_2COOH$ buffer was 6.0, reaction time was 10 hours, the concentration of $NaCNBH_3$ was re-optimized when the concentration of $NaCNBH_3$ was 0.02 mol/L, 0.03 mol/L, 0.04 mol/L and 0.05 mol/L, respectively. The results showed that when the concentration of $NaCNBH_3$ was decreased to 0.03 mol/L, the modification rate was equivalent to when $NaCNBH_3$ was 0.05 mol/L. When the concentration was decreased to 0.02 mol/L, the modification rate was significantly decreased. Therefore, the concentration of $NaCNBH_3$ was decreased to 0.03 mol/L. (4) Re-optimization of the conditions for mPEG-bALD modification of HM-1: 1) re-optimization of mPEG to HM-1 molar ratio: under the conditions of the reaction temperature was 4° C., peptide concentration was 1 mg/mL, $NaCNBH_3$ concentration was 0.05 mol/L, and the pH of the $CH_3COOH$—$NaCH_2COOH$ buffer was 6.0, the molar ratio of mPEG to HM-1 was re-optimized at a molar ratio of mPEG to HM-1 of 1.3:1, 1.4:1 and 1.5:1. The results showed that the product modification rate increased with the increase of mPEG and HM-1 molar ratio, but the difference was not obvious when the molar ratio was 1.4:1 and 1.5:1. For cost saving, the molar ratio was set to 1.4:1. 2) Re-optimization of $NaCNBH_3$ concentration: the re-optimization process and results are the same as mPEG-ALD modification of HM-1.

TABLE 3

Orthogonal Test Protocol for mPEG-SC modification of HM-1

| Test Group | Molar ratio of mPEG to HM-1 | Buffer pH | Reaction Time (h) |
|---|---|---|---|
| 1 | 1.1:1 | 7.5 | 1 |
| 2 | 1.1:1 | 8.0 | 2 |
| 3 | 1.1:1 | 8.5 | 3 |
| 4 | 1.3:1 | 7.5 | 2 |
| 5 | 1.3:1 | 8.0 | 3 |
| 6 | 1.3:1 | 8.5 | 1 |
| 7 | 1.5:1 | 7.5 | 3 |
| 8 | 1.5:1 | 8.0 | 1 |
| 9 | 1.5:1 | 8.5 | 2 |

TABLE 4

Orthogonal Test Protocol for $mPEG_2$-NHS modification of HM-1

| Test Group | Molar ration of mPEG toHM-1 | Buffer pH | Reaction Time (h) |
|---|---|---|---|
| 1 | 1.1:1 | 8.0 | 8 |
| 2 | 1.1:1 | 8.5 | 10 |
| 3 | 1.1:1 | 9.0 | 12 |
| 4 | 1.3:1 | 8.0 | 10 |
| 5 | 1.3:1 | 8.5 | 12 |
| 6 | 1.3:1 | 9.0 | 8 |
| 7 | 1.5:1 | 8.0 | 12 |
| 8 | 1.5:1 | 8.5 | 8 |
| 9 | 1.5:1 | 9.0 | 10 |

TABLE 5

Orthogonal Test Protocol for mPEG-ALD and mPEG-bALD modification of HM-1

| Test Group | Molar Ratio of mPEG to HM-1 | Buffer pH | Reaction Time (h) | Concentration of Reductant (mol/L) |
|---|---|---|---|---|
| 1 | 1.1:1 | 5.0 | 6 | 0.03 |
| 2 | 1.1:1 | 5.5 | 8 | 0.04 |
| 3 | 1.1:1 | 6.0 | 10 | 0.05 |
| 4 | 1.3:1 | 5.0 | 8 | 0.05 |
| 5 | 1.3:1 | 5.5 | 10 | 0.03 |
| 6 | 1.3:1 | 6.0 | 6 | 0.04 |
| 7 | 1.5:1 | 5.0 | 10 | 0.04 |
| 8 | 1.5:1 | 5.5 | 6 | 0.05 |
| 9 | 1.5:1 | 6.0 | 8 | 0.03 |

The exploration of rotary evaporation conditions: The main purpose of rotary evaporation is to remove the organic solvent in the solution and concentrate the solution. The two main factors affecting the rate of rotary evaporation and sample stability are temperature and time, and the length of time is also affected by temperature. Thus, we explored these two factors to raise the efficiency of concentrating step under conditions that ensure sample stability. Since the modified product in the solution state is sensitive to temperature, when the temperature is higher than 40° C., significant degradation occurs, so the temperature is set at 30-38° C., and the solution is concentrated to ⅓ of the original amount at different temperatures. The time required and the stability of the sample are shown in Table 6. The results showed that the time required for concentrating at 37° C. was shorter (40 min) and the stability of the sample was higher, so it was selected to carry out the rotary evaporation concentrating step at 37° C.

TABLE 6

Rotary Evaporation Conditions Exploration

| Test Group | Temperature (° C.) | Concentrating Time (min) | Sample Purity before Concentrating (%) | Sample Purity after Concentrating (%) |
|---|---|---|---|---|
| 1 | 30 | 132 | 98.9 | 98.2 |
| 2 | 31 | 125 | 99.1 | 98.4 |
| 3 | 32 | 115 | 99.0 | 98.5 |
| 4 | 33 | 100 | 98.8 | 98.2 |
| 5 | 34 | 85 | 98.9 | 98.2 |
| 6 | 35 | 70 | 98.5 | 98.2 |
| 7 | 36 | 55 | 98.8 | 98.6 |
| 8 | 37 | 40 | 99.0 | 98.9 |
| 9 | 38 | 30 | 98.7 | 97.8 |

The study found that the peptide with the sequence of Arg-Gly-Ala-Asp-Arg-Ala (SEQ ID NO: 3) has the effect of inhibiting tumor angiogenesis. The arginine-glycine-aspartate (RGD) sequence is an important ligand for integrin, therefore, the Gly-Gly-Gly-Gly-Arg-Gly-Asp (SEQ ID NO: 2) peptide containing the RGD sequence can also specifically recognize integrin. The angiogenesis inhibitor polypeptide of the present invention is a conjunction of the peptide Arg-Gly-Ala-Asp-Arg-Ala (SEQ ID NO: 3), which can inhibit angiogenesis, and the peptide Gly-Gly-Gly-Gly-Arg-Gly-Asp (SEQ ID NO: 2), which contains Arg-Gly-Asp (RGD) that has affinity towards and binds specifically to the integrin family, wherein the conjunction is at the C-terminal of the peptide Arg-Gly-Ala-Asp-Arg-Ala (SEQ ID NO: 3). The conjunction creates a polypeptide that has affinity towards and binding capacity for integrins, and inhibitory effect on angiogenesis. Meanwhile, the N-terminus of the angiogenesis inhibitory polypeptide with the integrin targeting capacity was specifically optimized by polyethylene glycol modification, and the final optimized sequence was: mPEG-Arg-Gly-Ala-Asp-Arg-Ala-Gly-Gly-Gly-Gly-Arg-Gly-Asp (SEQ ID NO: 1), which contains PEG and a 13 amino acid polypeptide. The target of the RGD sequence in the modified polypeptide is integrin $\alpha_v\beta_3$ and $\alpha_5\beta_1$, but the main binding target is still integrin $\alpha_v\beta_3$. Combined with neovascularization-inhibition sequence Arg-Gly-Ala-Asp-Arg-Ala (SEQ ID NO: 3), the polypeptides effectively inhibit tumor angiogenesis and thereby inhibits tumor growth and metastasis. Polyethylene glycol (PEG) is a type of macromolecular polymer with unique physicochemical properties. It is bio-compatible, non-toxic and non-antigenic. The main biological function of protein or peptide drugs after PEG modification remains unchanged, and PEG modification may confer protein a variety of desirable properties: (1) increase stability, prolonged plasma half-life; (2) reduced Immunogenicity and antigenicity; (3) reduced toxic side effects; (4) reduced possibility of degradation by hydrolase, reduced rate of removal by kidney; (5) improved drug distribution and kinetic behavior, etc.

The polypeptide HM-1 is modified by polyethylene glycol and the target is unchanged. At the same time, the in vivo half-life is prolonged, the clearance rate is reduced, immunogenicity and antigenicity are reduced, meanwhile the antitumor activity remains unchanged. As a result, the frequency of the drug administration is reduced, from once a day to once every 2-3 days for the PEG modified HM-1.

The inventors have discovered and disclosed through extensive experiments that the polyethylene glycol-modified angiogenesis inhibitor, i.e., the polypeptide, can significantly inhibit the proliferation and migration of human umbilical vein endothelial cells (HUVEC), and can significantly inhibit the proliferation of human cervical cancer HeLa cells, human colon cancer HCT 116 cells, human brain tumor cells U87 cells, human breast cancer cells MDA-MB-231, and other cancer cells.

The inventors have discovered and disclosed through extensive experiments that the polyethylene glycol-modified angiogenesis inhibitor can effectively treat angiogenesis inflammation. The experiments and test prove that the present invention can target the neovascular endothelium in the process of vasospasm formation in RA, inhibit the formation of new blood vessels, and thereby achieve the effect of preventing or treating rheumatoid arthritis. Furthermore, the current invention demonstrates, by the adjuvant type rat rheumatoid arthritis and the DBA/1 mouse collagen type rheumatoid arthritis model, that the current invention has remarkable effects of treating rheumatoid arthritis with less side effects, low dosage and low cost.

The inventors have discovered and disclosed through extensive experiments that the polyethylene glycol-modified angiogenesis inhibitor can inhibit the proliferation of human retinal vascular endothelial cells (HRCEC) in a dose-dependent manner within a range. The effect of angiogenesis inhibitor polypeptide on mouse corneal neovascularization and rabbit iris neovascularization indicates that the PEG-modified angiogenesis inhibitor of the present invention can inhibit the growth of cornea and iris neovascularization and has the potential to become a drug for treating corneal neovascular eye disease and iris neovascular eye disease, with the potential to treat other neovascular eye diseases.

The choroid is located in the posterior part of the eye. Our tests have shown that the angiogenesis inhibitors disclosed here can improve choroidal blood flow, indicating that the choroid can be reached presently after systemic circulation or scleral-uveal-optical nerve pathway after drug administration, thus the angiogenesis inhibitors can be used for the prevention or treatment of age-related macular degeneration (AMD) and other choroidal neovascular disease. At the same time, by inhibiting the formation of choroidal neovascularization in rats, it may have a certain therapeutic effect on choroidal neovascular diseases including age-related macular degeneration.

The polyethylene glycol-modified angiogenesis inhibitor designed by the invention is scientific, reasonable, feasible and effective, and can be used as a therapeutic drug for treating human tumors, various types of inflammation and neovascular eye diseases, and greatly expands the spectrum of diseases treatable by this class of angiogenesis inhibitor, providing new ideas and prospects for future drug development.

The half-life of the modified polypeptide HM-1 was 0.34 hour. The half-life of mPEG-HM-1 modified by polyethylene glycol is shown in Table 7.

TABLE 7

Comparison of Half-life of mPEG-HM-1 and HM-1 ($T_{1/2}\beta$ is half-life)

| Drug | $T_{1/2}\beta$ (h) | CL (L/h/kg) | $AUC_{0-\infty}$ (mg/L/h) | $MRT_{0-\infty}$ (h) |
|---|---|---|---|---|
| HM-1 | 0.34 ± 0.13 | 1..47 ± 0.31 | 32.79 ± 8.23 | 0.067 ± 0.013 |
| mPEG-SC$_{5k}$-HM-1 | 8.31 ± 0.12 | 0.0598 ± 0.0108 | 4391.72 ± 12.85 | 7.68 ± 2.97 |
| mPEG-SC$_{10k}$-HM-1 | 15.18 ± 0.11 | 0.0273 ± 0.0056 | 4671.86 ± 10.76 | 12.67 ± 5.84 |
| mPEG-SC$_{20k}$-HM-1 | 21.46 ± 0.24 | 0.0135 ± 0.0093 | 4310.23 ± 12.98 | 17.64 ± 12.67 |
| mPEG-SC$_{40k}$-HM-1 | 42.19 ± 0.32 | 0.0068 ± 0.0047 | 4365.64 ± 11.06 | 16.36 ± 10.28 |
| mPEG$_2$-NHS$_{5k}$-HM-1 | 8.85 ± 0.10 | 0.0527 ± 0.0112 | 4789.25 ± 12.08 | 8.02 ± 5.04 |
| mPEG$_2$-NHS$_{10k}$-HM-1 | 15.27 ± 0.11 | 0.0259 ± 0.0062 | 4858.62 ± 10.62 | 13.08 ± 3.66 |
| mPEG$_2$-NHS$_{20k}$-HM-1 | 22.38 ± 0.34 | 0.0131 ± 0.0102 | 4682.53 ± 15.01 | 18.16 ± 10.22 |
| mPEG$_2$-NHS$_{40k}$-HM-1 | 42.25 ± 0.27 | 0.0066 ± 0.0053 | 4579.47 ± 13.52 | 15.27 ± 9.37 |
| mPEG-ALD$_{5k}$-HM-1 | 9.13 ± 0.11 | 0.0506 ± 0.0094 | 4986.29 ± 10.16 | 8.15 ± 4.21 |
| mPEG-ALD$_{10k}$-HM-1 | 16.46 ± 0.10 | 0.0255 ± 0.0073 | 5067.98 ± 9.79 | 11.05 ± 7.68 |
| mPEG-ALD$_{20k}$-HM-1 | 22.65 ± 0.21 | 0.0129 ± 0.0106 | 5899.46 ± 6.68 | 18.65 ± 2.57 |
| mPEG-ALD$_{40k}$-HM-1 | 43.31 ± 0.22 | 0.0065 ± 0.0058 | 5276.69 ± 9.84 | 16.52 ± 3.06 |

TABLE 7-continued

Comparison of Half-life of mPEG-HM-1 and HM-1 ($T_{1/2}\beta$ is half-life)

| Drug | $T_{1/2}\beta$ (h) | CL (L/h/kg) | $AUC_{0-\infty}$ (mg/L/h) | $MRT_{0-\infty}$ (h) |
|---|---|---|---|---|
| mPEG-bALD$_{5k}$-HM-1 | 9.35 ± 0.12 | 0.0498 ± 0.0097 | 4782.29 ± 11.37 | 8.46 ± 6.95 |
| mPEG-bALD$_{10k}$-HM-1 | 16.83 ± 0.13 | 0.0250 ± 0.0105 | 5108.42 ± 9.98 | 11.97 ± 8.86 |
| mPEG-bALD$_{20k}$-HM-1 | 22.94 ± 0.24 | 0.0127 ± 0.0093 | 5872.56 ± 8.72 | 18.32 ± 2.99 |
| mPEG-bALD$_{40k}$-HM-1 | 43.88 ± 0.20 | 0.0066 ± 0.0066 | 5065.72 ± 9.56 | 16.75 ± 3.29 |

Beneficial Effects

Compared with the prior art, the beneficial effects of the present invention are:

(1) For protein polypeptide molecules, each amino acid change is a new molecule, which is a characteristic of biological macromolecules. Therefore, for biomacromolecules, including peptide molecules, none of the technologies are universal. It is necessary to explore and test to find out whether it is suitable for this new molecule; the polypeptide in the present invention is a brand-new molecule designed by the inventor, and is the first modification by polyethylene glycol, which requires a large number of experiments to obtain the desired effect, and cannot be realized by speculation. The product modified by polyethylene glycol (PEG) of the present invention also belongs to a novel molecule, and has different effects on the activity of the molecule before modification;

(2) For polypeptides, due to relative smaller molecular weight, modification with macromolecular PEG tends to cover its active site, resulting in reduced or complete loss of its activity; in addition, when the polypeptide is modified by PEG, it is unpredictable whether the problem of low modification rate or byproducts formation would occur. An ideal or adequate drug molecule, with intact activity and prolonged half-life, can only be acquired through selecting different PEG molecules, and the optimization and screening of different modification conditions. The present invention uses PEG having molecular weights of 5000, 10000, 20,000, and 40,000, respectively, to modify the polypeptide, and various conditions affecting the modification thereof, including: reaction temperature, reaction time, molar ratio of mPEG to HM-1, buffer type, the pH of the buffer, the concentration of the buffer, etc. are gradually optimized, and the modification reaction conditions with high modification rate and few by-products are selected.

(3) The types of PEG used for modifying the polypeptide HM-1 in the present invention are the mPEG-SC and mPEG$_2$-NHS used for the acylation the modified amino group, and mPEG-ALD and mPEG-bALD used for the alkylation of the modified amino group. Studies have shown that the biological activity of polypeptides were significantly reduced by PEG modification in general, and half-life was not necessarily prolonged. Different types and different molecular weights of PEG had different effects on the half-life and biological activity of HM-1. It is far from predictable to obtain the result of the present invention, whereon the polypeptide HM-1 was PEG-treated and after the modification, the modified product has a greatly prolonged half-life and the modified polypeptide HM-1 retains its original biological activity, as shown by extensive in vitro and in vivo pharmacodynamic tests.

(4) The present invention discloses novel molecules mPEG-HM-1, which is PEG-modified polypeptide HM-1. Extensive in vitro and in vivo activity studies were performed on the above four types of polyethylene glycol-modified angiogenesis inhibitor mPEG-HM-1 In the treatment of various diseases, it was found that various modified products maintained, sometimes even surpassed, the activity of HM-1, expanding its social and economic value.

DETAILED DESCRIPTION

The invention is further described below in conjunction with specific embodiments.

Example 1: Preparation and Test of Angiogenesis Inhibitor Polypeptide HM-1

The polypeptide HM-1 was synthesized by solid phase synthesis, isolated and purified by preparative HPLC, and its purity was determined by analytical RP-HPLC.

The solid phase synthesis method of polypeptide HM-1 is based on Fmoc-wang-resin or Fmoc-CTC-resin as starting material, subsequently protected amino acid were sequentially added to form the dipeptide, tripeptide, . . . to the thirteen amino acid peptide. After the peptide elongation is completed, the peptide was fully washed, cleaved, underwent post-processing to obtain a crude angiogenesis inhibitor product. The crude angiogenesis inhibitor product was dissolved, purified by preparative high-performance liquid phase twice, concentrated by lyophilization to obtain a pure product, and finally purified by a third purification to obtain a refined polypeptide product. This method not only ensures the efficiency of the synthesis, but also improves the purity of the product.

1. The steps for sequentially adding amino acids are as follows:

Weigh the appropriate amount of Fmoc-wang-resin or Fmoc-CTC-resin, pour into the glass sand core reaction column, and add $CH_2Cl_2$ to make the resin fully expand.

a. Uncapping: add an appropriate amount of uncapping solution of hexahydropyridine/DMF, let react for a period of time, drain the uncapping solution, washed once with DMF, and add a proper amount of the capping solution for a second time to react, remove the Fmoc protecting group;

b. Washing: drain the uncapping solution, wash the resin several times with DMF, and thoroughly wash the by-products;

c. connecting: the protected amino acid and activating reagent used for adding amino acid were dissolved in DMF and a condensing agent, mix well, the temperature was controlled at about 34° C., and fully reacted in the reaction vessel;

d. Washing: The reaction solution was drained, the resin was thoroughly washed with DMF, and the by-product was washed away.

2. The steps to cleave, or cut the peptide are as follows:

The dried resin was placed in a round bottom flask, the lysate was added to fully cleave the synthesized 13 amino acid peptide intermediary, and separate the cleaved polypeptide from the resin by a sand core funnel. The volume composition of the lysate was: trifluoroacetic acid: Phenol: Water: Benzyl sulfide: EDT=90:3:3:2:2.

3. The steps for post-processing are as follows:

The polypeptide was first precipitated by adding anhydrous ether to the cleave solution, then centrifuged, the supernatant was poured off, the polypeptide was washed with anhydrous diethyl ether and dried to obtain a crude polypeptide.

4. The steps for purification are as follows:

a. Dissolve: accurately weigh HM-1 crude product, add appropriate purified water to prepare a solution of 5-20 g/L, ultrasonically stir to a non-granular clear solution;

b. Filtration: The HM-1 crude solution was filtered through a sand filter 0.45 μm mixed filter;

c. Preparation: first purification, second purification and third purification by semi-preparative HPLC to obtain a purified peptide product, mobile phase: phase A was acetonitrile, phase B was 0.1% TFA in water.

①One-time purification: The column was prepared by 10% acetonitrile and 90% water (plus 0.1% TFA) at a flow rate of 60 mL/min, rinsed for 10 min, and loaded with an infusion pump. The elution gradient is shown in Table 8.

The first purification: The column was prepared by 10% acetonitrile and 90% water (plus 0.1% TFA) at a flow rate of 60 mL/min, rinsed for 10 min, and loaded with an infusion pump. The elution gradient is shown in Table 8.

TABLE 8

First Purification Elution Gradient

| Time (min) | Flow Rate (mL/min) | A % | B % | Wavelength (nm) |
|---|---|---|---|---|
| 0 | 60 | 10 | 90 | 220 |
| 40 | 60 | 20 | 80 | 220 |

Collect the solution having an absorption value greater than 200 mV at ultraviolet wavelength of 220 nm, combine aliquots with purity of more than 95% to use as peak top, which is to be subjected to the second purification.

②Second purification: the peak top was rotary evaporated to remove the organic solvent, balance a preparative column with a solution of 5% acetonitrile and 95% water (plus 0.1% TFA) at a flow rate of 60 mL/minutes, washing for 10 minutes, use the infusion pump to load. The elution gradient is shown in Table 9.

TABLE 9

Second Purification Elution Gradient

| Time (min) | Flow Rate (mL/min) | A % | B % | Wavelength (nm) |
|---|---|---|---|---|
| 0 | 60 | 5 | 95 | 220 |
| 40 | 60 | 15 | 85 | 220 |

Collect the solution having absorption value greater than 200 mV at an ultraviolet wavelength of 220 nm, combine aliquots with the purity greater than 98.5% as qualified product solution.

d. Concentration, filtration, lyophilization: The qualified product solution was concentrated under reduced pressure at 37° C. using a rotary evaporator to remove residual solvent and part of water. Finally, the solution was filtered through a 0.22 μm filter, the filtrate was placed in a lyophilized tray, and freeze-dried by a freeze dryer to obtain a pure product.

Example 2: Step of Modifying Polyethylene Glycol to HM-1

1), mPEG-SC modification of HM-1 steps

1. Reaction of mPEG-$SC_{5k}$ with HM-1

Weigh 0.25 g mPEG-$SC_{5k}$ and 40 mg HM-1 (1.5:1 molar ratio), place into 40 mL-100 mL of PBS buffer solution with pH 8.0-8.5, overnight at 4° C., let react.

2. Reaction of mPEG-$SC_{10k}$ with HM-1

Weigh 0.5 g of mPEG-$SC_{10k}$ and 40 mg of HM-1 (1.5:1 molar ratio), place into 40 mL-100 mL of PBS buffer solution of pH 8.0-8.5, overnight at 4° C., let react.

3. Reaction of mPEG-$SC_{20k}$ with HM-1

Weigh 1 g of mPEG-$SC_{20k}$ and 40 mg HM-1 (1.5:1 molar ratio), place into 40 mL-100 mL of PBS buffer solution of pH 8.0-8.5, overnight at 4° C., let react.

4. Reaction of mPEG-$SC_{40k}$ with HM-1

Weigh 2 g of mPEG-$SC_{40k}$ and 40 mg HM-1 (1.5:1 molar ratio), place them in 40 mL-100 mL of PBS buffer solution with pH 8.0-8.5, overnight at 4° C., let reacts. mPEG-SC having a molecular weight ranging from 500 to 40,000 can be subjected to ligation reaction to synthesize a modified polypeptide according to the present embodiment.

2), $mPEG_2$-NHS modification of HM-1 steps

1. Reaction of $mPEG_2$-$NHS_{5k}$ with HM-1

Weigh 0.25 g of $mPEG_2$-$NHS_{5k}$ and 40 mg of HM-1 (1.5:1 molar ratio) into 40 mL-100 mL of a boric acid buffer solution of pH 8.5-9.5, overnight at 4° C., let react.

2. Reaction of $mPEG_2$-$NHS_{10k}$ with HM-1

Weigh 0.5 g of $mPEG_2$-$NHS_{10k}$ and 40 mg of HM-1 (1.5:1 molar ratio) and place them in 40 mL-100 mL of boric acid buffer solution with pH 8.5-9.5, overnight at 4° C., let react.

3. Reaction of $mPEG_2$-$NHS_{20k}$ with HM-1

Weigh 1 g of $mPEG_2$-$NHS_{20k}$ and 40 mg of HM-1 (1.5:1 molar ratio) and place them in 40 mL-100 mL of boric acid buffer solution with pH 8.5-9.5, overnight at 4° C., let react.

4. Reaction of $mPEG_2$-$NHS_{40k}$ with HM-1

Weigh 2 g of $mPEG_2$-$NHS_{40k}$ and 40 mg of HM-1 (1.5:1 molar ratio) and place them in 40 mL-100 mL of boric acid buffer solution with pH 8.5-9.5, overnight at 4° C., let react. The $mPEG_2$-NHS having a molecular weight ranging from 500 to 40,000 can be subjected to a ligation reaction to synthesize a modified polypeptide according to the present embodiment.

3), mPEG-ALD modification of HM-1 steps

1. Reaction of mPEG-$ALD_{5k}$ with HM-1

Weigh 0.25 g mPEG-$ALD_{5k}$, 40 mg HM-1 (1.5:1 molar ratio) and 126.2 mg sodium cyanoborohydride ($NaCNBH_3$) in 40 mL-100 mL PBS buffered at pH 5.0-6.0. The solution was allowed to react sufficiently at 4° C. overnight.

2. Reaction of mPEG-$ALD_{10k}$ with HM-1

Weigh 0.5 g mPEG-$ALD_{10k}$, 40 mg HM-1 (1.5:1 molar ratio) and 126.2 mg $NaCNBH_3$ in 40 mL-100 mL PBS buffer solution at pH 5.0-6.0 at 4° C. Leave it overnight and allow it to react adequately.

3. Reaction of mPEG-$ALD_{20k}$ with HM-1

Weigh 1 g of mPEG-$ALD_{20k}$, 40 mg of HM-1 (1.5:1 molar ratio) and 126.2 mg of sodium cyanoborohydride ($NaCNBH_3$) in 40 mL-100 mL of PBS buffered with pH 5.0-6.0. The solution was allowed to react sufficiently at 4° C. overnight.

4. Reaction of mPEG-$ALD_{40k}$ with HM-1

Weigh 2 g mPEG-$ALD_{40k}$, 40 mg HM-1 (1.5:1 molar ratio) and 126.2 mg sodium cyanoborohydride ($NaCNBH_3$)

in 40 mL-100 mL PBS buffered with pH 5.0-6.0. The solution was allowed to react sufficiently at 4° C. overnight. The mPEG-ALD having a molecular weight in the range of 500 to 40,000 can be subjected to a ligation reaction to synthesize a modified polypeptide according to the present embodiment.

4), mPEG-bALD modification of HM-1 steps

1. Reaction of mPEG-bALD$_{5k}$ with HM-1

Weigh 0.25 g mPEG-bALD$_{5k}$, 40 mg HM-1 (1.5:1 molar ratio) and 126.2 mg sodium cyanoborohydride (NaCNBH$_3$) in 40 mL-100 mL PBS buffered with pH 5.0-6.0. The solution was allowed to react sufficiently at 4° C. overnight.

2. Reaction of mPEG-bALD$_{10k}$ with HM-1

Weigh 0.5 g mPEG-bALD$_{10k}$, 40 mg HM-1 (1.5:1 molar ratio) and 126.2 mg sodium cyanoborohydride (NaCNBH$_3$) in 40 mL-100 mL PBS buffered with pH 5.0-6.0. The solution was allowed to react sufficiently at 4° C. overnight.

3. Reaction of mPEG-bALD$_{20k}$ with HM-1

Weigh 1 g mPEG-bALD$_{20k}$, 40 mg HM-1 (molar ratio 1.5:1 0 and 126.2 mg sodium cyanoborohydride (NaCNBH$_3$) in 40 mL-100 mL PBS buffered with pH 5.0-6.0 The solution was allowed to react sufficiently at 4° C. overnight.

4. Reaction of mPEG-bALD$_{40k}$ with HM-1

Weigh 2 g mPEG-bALD$_{40k}$, 40 mg HM-1 (1.5:1 molar ratio) and 126.2 mg sodium cyanoborohydride (NaCNBH$_3$) in 40 mL-100 mL PBS buffered with pH 5.0-6.0. The solution was allowed to react sufficiently at 4° C. overnight. mPEG-bALD having a molecular weight ranging from 500 to 40,000 can be subjected to a ligation reaction to synthesize a modified polypeptide according to the present embodiment.

Example 3: Separation and Purification Steps of Polyethylene Glycol-Modified HM-1

1), separation or isolation

The sample after the reaction was purified by semi-preparative high performance liquid chromatography (HPLC, Beijing Chuangxintongheng). The purification conditions were as follows:

Semi-preparative column: YMC, 250 mm×20 mm (5 μm packing);

Mobile phase: phase A is acetonitrile and phase B is water;

Loading amount: 5 mL;

Flow rate: 15 mL/min;

Detection wavelength: 220 nm;

Elution gradient: elution gradients of mPEG-SC$_{5k}$-HM-1, mPEG$_2$-NHS$_{5k}$-HM-1, mPEG-ALD$_{5k}$-HM-1 and mPEG-bALD$_{5k}$-HM-1 were shown in elution gradient 1 (Table 10); elution gradients of mPEG-SC$_{10k}$-HM-1, mPEG$_2$-NHS$_{10k}$-HM-1, mPEG-ALD$_{10k}$-HM-1 and mPEG-bALD$_{10k}$-HM-1 were shown in elution gradient 2 (Table 11); Elution gradients of mPEG-SC$_{20k}$-HM-1, mPEG$_2$-NHS$_{20k}$-HM-1, mPEG-ALD$_{20k}$-HM-1 and mPEG-bALD$_{20k}$-HM-1 were shown in elution gradient 3 (Table 12); elution gradients of mPEG-SC$_{40k}$-HM-1, mPEG$_2$-NHS$_{40k}$-HM-1, mPEG-ALD$_{40k}$-HM-1 and mPEG-bALD$_{40k}$-HM-1 were shown in elution gradient 4 (Table 13).

TABLE 10

Elution Gradient 1

| Time (min) | Flow Rate (mL/min) | A % | B % | Wavelength (nm) |
|---|---|---|---|---|
| 0 | 15 | 5 | 95 | 220 |
| 10 | 15 | 10 | 90 | 220 |
| 30 | 15 | 55 | 45 | 220 |

TABLE 11

Elution Gradient 2

| Time (min) | Flow Rate (mL/min) | A % | B % | Wavelength (nm) |
|---|---|---|---|---|
| 0 | 15 | 5 | 95 | 220 |
| 10 | 15 | 10 | 90 | 220 |
| 30 | 15 | 65 | 35 | 220 |

TABLE 12

Elution Gradient 3

| Time (min) | Flow Rate (mL/min) | A % | B % | Wavelength (nm) |
|---|---|---|---|---|
| 0 | 15 | 5 | 95 | 220 |
| 10 | 15 | 10 | 90 | 220 |
| 30 | 15 | 75 | 25 | 220 |

TABLE 13

Elution Gradient 4

| Time (min) | Flow Rate (mL/min) | A % | B % | Wavelength (nm) |
|---|---|---|---|---|
| 0 | 15 | 5 | 95 | 220 |
| 10 | 15 | 10 | 90 | 220 |
| 30 | 15 | 85 | 15 | 220 |

When target peak was eluted, the product was collected using a centrifuge tube.

2), purification

The product collected by semi-preparative HPLC was first pre-freezed overnight in a 70° C. low temperature freezer, and then lyophilized in a pre-cooled freeze dryer until all white powder was visually observed (about 30 hours). The lyophilized product was harvested, the weight of the product was weighed and recorded, and stored in a refrigerator at −20° C. and identified.

1. Purity Analysis of the Product

The product after lyophilization was analyzed for purity by analytical HPLC, and the analysis conditions were as follows:

Analytical column: COSMOSIL, 250 mm×4.6 mm (5 μm packing);

Mobile phase: phase A was water (plus 0.1% TFA), phase B was acetonitrile (plus 0.1% TFA);

Loading amount: 20 μL;

Flow rate: 1 mL/min;

Detection wavelength: 220 nm;

Elution gradient: see Table 14.

TABLE 14

| Time (min) | Flow Rate (mL/min) | A % | B % | Wavelength nm |
|---|---|---|---|---|
| 0 | 1 | 80 | 20 | 220 |
| 40 | 1 | 15 | 85 | 220 |

2. SDS-PAGE Analysis of Modified Products

For basic operations, refer to Molecular Cloning (Second Edition). The concentration of the concentrated gel was 5%, the separation gel concentration was 15%, the concentration voltage was 80 volts, and the separation voltage was 120 volts. After electrophoresis, the sample strip was first stained with Coomassie Brilliant Blue R250. After staining, it was placed in the decolorizing solution until the background was transparent, and then scanned and analyzed. Then, the part containing PEG was stained with $BaI_2$, and the staining was completed and decolorized in water. The background is transparent and scanned for analysis.

Example 4: Proliferation Inhibition Test of Polyethylene Glycol-Modified Angiogenesis Inhibitor Polypeptide (mPEG-HM-1) on Various Tumor Cells The activity of mPEG-HM-1 to inhibit the growth of various tumor cells was examined by MTT assay. The tumor cells were cultured to a concentration of 90% or more in a 37° C., 5% $CO_2$ incubator and collected by trypsinization. The cells were resuspended in the culture medium and counted under a microscope to adjust the cell concentration to $2 \times 10^4$ cells/mL, the cell suspension was inoculated into a 96-well plate at 100 μL/well and incubated overnight at 37° C. in a 5% $CO_2$ incubator. mPEG-HM-1 was diluted with the culture solution to each predetermined concentration. Docetaxel is diluted to the final concentration with the culture medium. After the cells were fully attached, each dilution was added to a 96-well plate (100 μL/well). The mPEG-HM-1 dilution was added as a drug-administered group, and docetaxel was added as a positive control group, and a culture solution without any drug was used as a negative control group. Incubate for 48 h at 37° C. in a 5% $CO_2$ incubator. 5 mg/mL of MTT was added to a 96-well plate at 20 μL per well, and incubation was continued for 4 hours. The medium was aspirated, dissolved in 150 μL of DMSO per well, and gently mixed by shaking for 10 min. The absorbance was measured at a measurement wavelength of 570 nm and a reference wavelength of 630 nm using a microplate reader, and the rate of growth inhibition (proliferation inhibition, PI) was calculated. The formula is as follows:

PI (%)=1−administration group/negative group

The test was repeated 3 times independently, and the results obtained by the test were expressed as mean±SD, and the test results are shown in Table 15 to Table 18.

TABLE 15 mPEG-SC-HM-1 rate of growth inhibition on various tumor cells (%)

| Source of Tumor Cells | mPEG-$SC_{5k}$-HM-1 | mPEG-$SC_{10k}$-HM-1 | mPEG-$SC_{20k}$-HM-1 | mPEG-$SC_{40k}$-HM-1 | Docetaxel |
|---|---|---|---|---|---|
| Head and neck cancer | 40.27 ± 11.36 | 45.61 ± 11.12 | 49.26 ± 10.32 | 43.22 ± 10.25 | 49.23 ± 10.01 |
| Brain tumor | 42.18 ± 12.29 | 50.21 ± 12.19 | 55.56 ± 12.13 | 52.89 ± 15.41 | 59.23 ± 16.21 |
| Thyroid cancer | 39.23 ± 13.18 | 46.23 ± 13.05 | 50.78 ± 13.46 | 50.13 ± 14.21 | 56.21 ± 14.28 |
| Esophageal cancer | 44.38 ± 10.72 | 52.18 ± 10.25 | 55.51 ± 16.22 | 52.12 ± 12.35 | 60.18 ± 17.02 |
| Pancreatic cancer | 51.37 ± 16.23 | 60.53 ± 17.16 | 62.63 ± 18.13 | 60.45 ± 17.25 | 71.13 ± 20.13 |
| Lung cancer | 45.33 ± 12.67 | 50.29 ± 13.18 | 53.87 ± 15.66 | 51.32 ± 16.29 | 68.23 ± 18.32 |
| Liver cancer | 51.34 ± 11.25 | 57.18 ± 12.35 | 61.09 ± 14.09 | 60.37 ± 14.74 | 66.70 ± 17.25 |
| Gastric cancer | 52.12 ± 13.22 | 56.22 ± 16.19 | 66.14 ± 20.08 | 55.13 ± 10.32 | 77.34 ± 22.18 |
| Breast cancer | 48.13 ± 12.17 | 50.16 ± 13.27 | 52.18 ± 18.28 | 50.12 ± 18.09 | 65.31 ± 21.44 |
| Kidney cancer | 51.07 ± 12.45 | 60.07 ± 14.24 | 67.29 ± 18.16 | 62.23 ± 16.51 | 72.93 ± 18.31 |
| Colorectal cancer | 55.35 ± 12.82 | 61.35 ± 16.88 | 66.19 ± 20.58 | 62.45 ± 19.22 | 74.59 ± 20.33 |
| Ovarian cancer | 60.81 ± 20.27 | 65.89 ± 23.37 | 70.94 ± 20.65 | 68.46 ± 13.19 | 85.12 ± 19.39 |
| Cervical cancer | 51.11 ± 16.20 | 57.17 ± 18.40 | 62.93 ± 20.09 | 61.52 ± 15.11 | 80.21 ± 19.54 |
| Uterine cancer | 60.25 ± 16.09 | 65.29 ± 19.06 | 76.93 ± 23.14 | 70.27 ± 21.37 | 80.25 ± 22.18 |
| Prostate cancer | 38.37 ± 15.61 | 45.39 ± 12.63 | 49.35 ± 10.04 | 45.93 ± 12.72 | 45.62 ± 14.03 |
| Bladder Cancer | 35.72 ± 11.52 | 42.76 ± 10.06 | 50.39 ± 11.73 | 48.69 ± 11.61 | 46.72 ± 13.65 |
| Melanoma | 61.27 ± 18.13 | 70.62 ± 20.17 | 72.14 ± 20.69 | 68.73 ± 21.25 | 83.49 ± 23.27 |
| Hemangioma | 43.68 ± 12.53 | 52.88 ± 13.66 | 55.63 ± 18.30 | 53.36 ± 15.09 | 56.92 ± 16.76 |
| sarcoma | 39.42 ± 11.15 | 45.49 ± 11.89 | 48.93 ± 10.53 | 45.26 ± 11.61 | 51.31 ± 10.49 |

Results: Compared with the negative control, mPEG-SC-HM-1 significantly inhibited the proliferation of various tumor cells. Among them, mPEG-SC$_{20k}$-HM-1 had the best effect and inhibited the proliferation of some tumor cells at a level that is close to the positive drug. These results also provided a basis for developing even more effective antitumor drugs.

TABLE 16 mPEG$_2$-NHS-HM-1 rate of growth inhibition on various tumor cells (%)

| Source of Tumor cells | mPEG$_2$-NHS$_{5k}$-HM-1 | mPEG$_2$-NHS$_{10k}$-HM-1 | mPEG$_2$-NHS$_{20k}$-HM-1 | mPEG$_2$-NHS$_{40k}$-HM-1 | Docetaxel |
|---|---|---|---|---|---|
| Head and neck cancer | 37.13 ± 11.32 | 43.52 ± 11.16 | 46.18 ± 11.22 | 40.36 ± 10.53 | 49.23 ± 10.01 |
| Brain tumor | 40.35 ± 10.29 | 47.62 ± 11.11 | 45.51 ± 10.15 | 42.56 ± 11.38 | 59.23 ± 16.21 |
| Thyroid cancer | 36.23 ± 12.15 | 40.47 ± 12.03 | 43.68 ± 13.61 | 45.19 ± 14.07 | 56.21 ± 14.28 |
| Esophageal cancer | 41.35 ± 11.32 | 48.12 ± 12.85 | 50.79 ± 14.37 | 48.65 ± 12.64 | 60.18 ± 17.02 |
| Pancreatic cancer | 46.58 ± 13.12 | 50.23 ± 14.26 | 52.13 ± 13.32 | 51.49 ± 16.28 | 71.13 ± 20.13 |
| Lung cancer | 42.83 ± 12.58 | 45.28 ± 13.96 | 50.82 ± 12.68 | 49.39 ± 16.55 | 68.23 ± 18.32 |
| Liver cancer | 50.92 ± 11.66 | 54.19 ± 12.80 | 55.03 ± 14.19 | 53.77 ± 13.64 | 66.70 ± 17.25 |
| Gastric cancer | 50.31 ± 13.29 | 55.67 ± 13.53 | 60.90 ± 20.14 | 56.39 ± 11.58 | 77.34 ± 22.18 |
| Breast cancer | 45.69 ± 12.10 | 50.92 ± 13.97 | 52.68 ± 17.25 | 49.12 ± 16.19 | 65.31 ± 21.44 |
| Kidney cancer | 47.52 ± 11.48 | 52.09 ± 14.91 | 55.20 ± 15.43 | 58.73 ± 14.31 | 72.93 ± 18.31 |
| Colorectal cancer | 52.37 ± 12.24 | 55.78 ± 15.77 | 58.16 ± 20.36 | 54.40 ± 18.29 | 74.59 ± 20.33 |
| Ovarian cancer | 56.88 ± 21.07 | 60.69 ± 21.24 | 63.55 ± 19.60 | 61.59 ± 13.61 | 85.12 ± 19.39 |
| Cervical cancer | 49.15 ± 14.23 | 54.82 ± 17.10 | 60.63 ± 19.39 | 57.33 ± 14.28 | 80.21 ± 19.54 |
| Uterine cancer | 55.20 ± 15.63 | 60.49 ± 18.05 | 65.99 ± 22.07 | 62.25 ± 20.39 | 80.25 ± 22.18 |
| Prostate cancer | 39.33 ± 12.01 | 42.39 ± 12.65 | 47.75 ± 10.14 | 45.91 ± 11.74 | 45.62 ± 14.03 |
| Bladder Cancer | 38.64 ± 12.72 | 43.78 ± 10.16 | 49.79 ± 12.73 | 45.60 ± 10.11 | 46.72 ± 13.65 |
| Melanoma | 59.21 ± 18.93 | 65.89 ± 20.57 | 69.11 ± 21.79 | 66.72 ± 20.85 | 83.49 ± 23.27 |
| Hemangioma | 42.78 ± 12.50 | 48.81 ± 12.46 | 55.38 ± 16.23 | 50.64 ± 15.89 | 56.92 ± 16.76 |
| sarcoma | 38.41 ± 11.10 | 43.59 ± 12.39 | 48.91 ± 10.57 | 46.46 ± 11.54 | 51.31 ± 10.49 |

Results: Compared with the negative control, mPEG$_2$-NHS-HM-1 inhibited the proliferation of various tumor cells. Among them, mPEG$_2$-NHS$_{20k}$-HM-1 had the best effect, but to most of the tumor cells tested here, the inhibitory effect of mPEG-SC$_{20k}$-HM-1 is superior to that of mPEG$_2$-NHS$_{20k}$-HM-1, which provides a reference for further development of antitumor drugs.

TABLE 17 mPEG-ALD-HM-1 rate of growth inhibition on various tumor cells (%)

| Source of Tumor cells | mPEG-ALD$_{5k}$-HM-1 | mPEGALD$_{10k}$-HM-1 | mPEG-ALD$_{20k}$-HM-1 | mPEG-ALD$_{40k}$-HM-1 | Docetaxel |
|---|---|---|---|---|---|
| Head and neck cancer | 40.71 ± 11.33 | 48.93 ± 12.14 | 47.61 ± 10.68 | 42.18 ± 10.01 | 49.23 ± 10.01 |
| Brain tumor | 42.15 ± 12.89 | 58.25 ± 14.02 | 56.89 ± 15.41 | 50.69 ± 14.41 | 59.23 ± 16.21 |
| Thyroid cancer | 40.23 ± 10.05 | 55.30 ± 13.10 | 50.35 ± 15.23 | 49.03 ± 13.08 | 56.21 ± 14.28 |
| Esophageal cancer | 44.63 ± 10.86 | 65.18 ± 15.16 | 60.18 ± 15.32 | 58.11 ± 14.67 | 60.18 ± 17.02 |
| Pancreatic cancer | 52.19 ± 12.64 | 79.21 ± 19.14 | 70.65 ± 20.29 | 65.31 ± 19.81 | 71.13 ± 20.13 |
| Lung cancer | 45.76 ± 13.20 | 65.73 ± 16.20 | 66.38 ± 17.16 | 55.44 ± 16.13 | 68.23 ± 18.32 |
| Liver cancer | 52.98 ± 11.55 | 70.55 ± 20.09 | 65.31 ± 18.18 | 60.78 ± 10.88 | 66.70 ± 17.25 |
| Gastric cancer | 58.77 ± 15.49 | 80.01 ± 18.26 | 75.23 ± 20.62 | 70.66 ± 18.72 | 77.34 ± 22.18 |
| Breast cancer | 49.22 ± 11.87 | 70.19 ± 17.07 | 65.17 ± 18.20 | 60.17 ± 19.24 | 65.31 ± 21.44 |
| Kidney cancer | 55.43 ± 14.04 | 75.23 ± 19.11 | 70.23 ± 20.58 | 68.46 ± 20.98 | 72.93 ± 18.31 |
| Colorectal cancer | 57.30 ± 15.82 | 80.22 ± 20.03 | 72.43 ± 19.32 | 70.92 ± 16.52 | 74.59 ± 20.33 |
| Ovarian cancer | 65.81 ± 20.42 | 85.73 ± 22.17 | 80.68 ± 21.69 | 74.61 ± 20.09 | 85.12 ± 19.39 |
| Cervical cancer | 61.12 ± 18.39 | 83.04 ± 18.74 | 75.66 ± 20.10 | 70.62 ± 19.14 | 80.21 ± 19.54 |
| Uterine cancer | 65.99 ± 17.72 | 90.79 ± 22.19 | 89.37 ± 23.47 | 82.59 ± 21.37 | 80.25 ± 22.18 |
| Prostate cancer | 38.47 ± 11.52 | 51.09 ± 11.78 | 43.99 ± 12.77 | 42.91 ± 11.65 | 45.62 ± 14.03 |
| Bladder Cancer | 35.93 ± 10.29 | 52.68 ± 13.12 | 45.29 ± 11.63 | 43.22 ± 10.31 | 46.72 ± 13.65 |
| Melanoma | 63.61 ± 21.30 | 88.39 ± 22.38 | 80.71 ± 23.46 | 75.18 ± 21.75 | 83.49 ± 23.27 |
| Hemangioma | 43.89 ± 14.14 | 60.25 ± 14.33 | 53.30 ± 16.06 | 50.67 ± 14.02 | 56.92 ± 16.76 |
| sarcoma | 38.41 ± 12.53 | 53.01 ± 11.42 | 50.96 ± 11.68 | 45.93 ± 10.77 | 51.31 ± 10.49 |

Results: Compared with the negative control, mPEG-ALD-HM-1 significantly inhibited the proliferation of various tumor cells, of which mPEG-ALD$_{10k}$-HM-1 had the best effect and was superior to mPEG-SC-HM-1 and mPEG$_2$-NHS-HM-1. mPEG-ALD$_{10k}$-HM-1 has more potent inhibitory effects on the proliferation of some tumor cells compared to the positive control, which provides a good prospect for the development of an effective anti-tumor drug.

$$MI(\%) = 1 - \frac{N_{test}}{N_{control}} \times 100\%$$

$N_{test}$ was the number of cell migration in the test group, and $N_{control}$ was the number of cell migration in the blank control group.

TABLE 18 mPEG-bALD-HM-1 rate of growth inhibition on various tumor cells (%)

| Source of Tumor cells | mPEG-bALD$_{5k}$-HM-1 | mPEG-bALD$_{10k}$-HM-1 | mPEG-bALD$_{20k}$-HM-1 | mPEG-bALD$_{40k}$-HM-1 | Docetaxel |
|---|---|---|---|---|---|
| Head and neck cancer | 39.92 ± 11.33 | 49.01 ± 12.14 | 45.13 ± 12.38 | 40.09 ± 12.02 | 49.23 ± 10.01 |
| Brain tumor | 45.11 ± 12.09 | 59.37 ± 14.52 | 54.77 ± 13.43 | 51.89 ± 11.91 | 59.23 ± 16.21 |
| Thyroid cancer | 42.19 ± 10.35 | 55.74 ± 13.13 | 49.38 ± 13.20 | 45.53 ± 12.98 | 56.21 ± 14.28 |
| Esophageal cancer | 45.03 ± 11.46 | 64.92 ± 12.17 | 60.56 ± 14.72 | 57.19 ± 12.07 | 60.18 ± 17.02 |
| Pancreatic cancer | 53.14 ± 10.34 | 75.23 ± 16.41 | 69.54 ± 18.37 | 62.85 ± 18.74 | 71.13 ± 20.13 |
| Lung cancer | 47.56 ± 12.22 | 66.72 ± 14.42 | 65.31 ± 15.54 | 56.47 ± 14.15 | 68.23 ± 18.32 |
| Liver cancer | 55.63 ± 10.27 | 68.59 ± 20.19 | 62.49 ± 16.14 | 58.72 ± 10.80 | 66.70 ± 17.25 |
| Gastric cancer | 56.87 ± 14.41 | 75.01 ± 16.20 | 70.21 ± 18.32 | 68.65 ± 16.93 | 77.34 ± 22.18 |
| Breast cancer | 50.02 ± 10.47 | 68.15 ± 15.87 | 60.97 ± 16.29 | 62.45 ± 19.04 | 65.31 ± 21.44 |
| Kidney cancer | 57.63 ± 12.09 | 70.19 ± 18.11 | 66.81 ± 19.48 | 60.06 ± 18.88 | 72.93 ± 18.31 |
| Colorectal cancer | 59.35 ± 12.64 | 75.62 ± 18.03 | 70.73 ± 16.92 | 66.90 ± 16.27 | 74.59 ± 20.33 |
| Ovarian cancer | 66.76 ± 18.59 | 80.35 ± 20.53 | 75.65 ± 20.09 | 72.66 ± 19.03 | 85.12 ± 19.39 |
| Cervical cancer | 64.52 ± 16.88 | 80.08 ± 18.34 | 78.57 ± 20.11 | 70.34 ± 19.04 | 80.21 ± 19.54 |
| Uterine cancer | 65.46 ± 18.52 | 79.79 ± 20.45 | 75.97 ± 22.67 | 70.51 ± 20.22 | 80.25 ± 22.18 |
| Prostate cancer | 39.27 ± 12.50 | 50.02 ± 10.65 | 46.90 ± 11.54 | 40.82 ± 11.75 | 45.62 ± 14.03 |
| Bladder Cancer | 36.03 ± 10.12 | 49.61 ± 12.12 | 45.24 ± 10.69 | 43.82 ± 10.31 | 46.72 ± 13.65 |
| Melanoma | 65.62 ± 20.35 | 82.33 ± 20.08 | 80.75 ± 22.94 | 73.10 ± 20.55 | 83.49 ± 23.27 |
| Hemangioma | 40.29 ± 12.16 | 55.28 ± 12.30 | 50.31 ± 14.00 | 48.69 ± 12.72 | 56.92 ± 16.76 |
| sarcoma | 41.42 ± 10.03 | 52.01 ± 12.32 | 50.91 ± 10.64 | 47.90 ± 10.70 | 51.31 ± 10.49 |

Results: compared with the negative control, mPEG-bALD-HM-1 significantly inhibited the proliferation of various tumor cells. Among them, mPEG-bALD$_{10k}$-HM-1 had the best effect, and its inhibition was comparable to mPEG-ALD$_{10k}$-HM-1. These results also provided a good prospect for the development of an anti-tumor drug for the present invention.

Example 5: Inhibition of Migration of Human Umbilical Vein Endothelial Cells (HUVEC) by mPEG-HM-1

10 mg/mL Matrigel was diluted 1:2 with HUVEC-specific medium, spread on a transwell chamber membrane, and air-dried at room temperature. HUVEC cells cultured in logarithmic growth phase were digested with trypsin digest, collected, washed twice with PBS, and resuspended in blank HUVECs-specific medium. The cells were counted under a microscope, and the cell concentration was adjusted to 1×10$^5$/mL. The test solutions of each group were prepared and diluted to 100 µL with a blank HUVECs-specific medium. The cells were seeded into a transwell chamber at 100 µL per well, and each set of test solution was added to the chamber. The cell culture was stimulated by adding 0.6 mL of endothelial cell culture medium containing 5% fetal bovine serum and 1% ECGS into a 24-well plate, and cultured at 5% CO$_2$ for 24 hour at 37° c. Discard the culture medium in the well, fix it with 90% alcohol at room temperature for 30 minutes, 0.1% crystal violet for 10 min at room temperature, rinse with water, gently wipe off the unsprayed cells in the upper layer with a cotton swab, observe under microscope and select four fields to take pictures. Calculate migration inhibition (MI) according to the formula:

The test was repeated 3 times independently. The results obtained from the test were calculated as mean±SD, and a statistical T test was performed. *P<0.05 was a significant difference, and **P<0.01 was a very significant difference. The test results are shown in Tables 19 to 22.

TABLE 19 mPEG-SC-HM-1 Inhibition of HUVEC migration

| Groups | Doses (µg/mL) | cell migration number (Mean ± SD) | inhibition rate (%) |
|---|---|---|---|
| mPEG-SC$_{5k}$-HM-1 | 30 | 617.03 ± 60.97 | 41.83%* |
|  | 40 | 517.43 ± 50.39 | 51.22%** |
|  | 50 | 469.59 ± 48.95 | 55.73%** |
|  | 60 | 601.65 ± 60.73 | 43.28%* |
| mPEG-SC$_{10k}$-HM-1 | 50 | 612.15 ± 50.34 | 42.49%* |
|  | 60 | 527.08 ± 48.30 | 50.31%** |
|  | 70 | 439.89 ± 48.08 | 58.53%** |
|  | 80 | 580.33 ± 58.20 | 45.29%* |
| mPEG-SC$_{20k}$-HM-1 | 70 | 596.77 ± 50.58 | 43.74%* |
|  | 80 | 499.29 ± 50.26 | 52.93%** |
|  | 90 | 415.07 ± 46.74 | 60.87%** |
|  | 100 | 559.75 ± 52.94 | 47.23%* |
| mPEG-SC$_{40k}$-HM-1 | 90 | 632.63 ± 58.69 | 40.36%* |
|  | 100 | 501.84 ± 62.84 | 52.69%** |
|  | 110 | 464.50 ± 48.47 | 56.21%** |
|  | 120 | 542.89 ± 49.29 | 48.82%* |
| Avastin | 10 | 564.53 ± 60.36 | 46.78%* |
| control | — | 1060.74 ± 32.65 | 0.00% |

Results: Under the action of mPEG-SC-HM-1, the number of migrated endothelial cells was significantly reduced. Compared with the blank control group, it inhibited the migration of HUVEC induced by 5% fetal bovine serum and 1% ECGS. The inhibition of cell migration by mPEG-SC$_{5k}$-HM-1 at 40 µg/mL and 50 µg/mL was significantly different from that of the blank control (P<0.01), and the inhibition rate reached 51.22.% and 55.73%; the inhibition of cell migration by mPEG-SC$_{10k}$-HM-1 at 60 µg/mL and 70 µg/mL was significantly different from that of the blank control (P<0.01). The inhibition rates reached 50.31% and 58.53%, respectively; the inhibition of cell migration by mPEG-SC$_{20k}$-HM-1 at 80 µg/mL and 90 µg/mL was significantly different from that of the blank control ( P<0.01), the inhibition rates reached 52.93% and 60.87%, respectively; the inhibition of cell migration by mPEG-SC$_{40k}$-HM-1 at 100 µg/mL and 110 µg/mL was extremely significant compared with the blank control. Sexual differences (P<0.01), the inhibition rates reached 52.69% and 56.21%, respectively.

TABLE 20 mPEG$_2$-NHS-HM-1 Inhibition of HUVEC migration

| Groups | Doses (µg/mL) | cell migration number (Mean ± SD) | inhibition rate (%) |
|---|---|---|---|
| mPEG$_2$-NHS$_{5k}$-HM-1 | 30 | 611.33 ± 58.92 | 41.03%* |
|  | 40 | 516.16 ± 48.34 | 50.21%** |
|  | 50 | 475.01 ± 50.90 | 54.18%** |
|  | 60 | 590.29 ± 50.72 | 43.06%* |
| mPEG$_2$-NHS$_{10k}$-HM-1 | 50 | 603.97 ± 40.36 | 41.74%* |
|  | 60 | 506.83 ± 46.25 | 51.11%** |
|  | 70 | 410.53 ± 48.64 | 60.40%** |
|  | 80 | 563.02 ± 56.22 | 45.69%* |
| mPEG$_2$-NHS$_{20k}$-HM-1 | 70 | 618.48 ± 47.53 | 40.34%* |
|  | 80 | 512.85 ± 40.86 | 50.53%** |
|  | 90 | 434.68 ± 42.64 | 58.07%** |
|  | 100 | 562.61 ± 62.34 | 45.73%* |
| mPEG$_2$-NHS$_{40k}$-HM-1 | 90 | 640.05 ± 50.70 | 38.26%* |
|  | 100 | 516.99 ± 60.04 | 50.13%** |
|  | 110 | 464.43 ± 46.48 | 55.20%** |
|  | 120 | 584.48 ± 52.28 | 43.62%* |
| Avastin | 10 | 560.64 ± 62.06 | 45.92%* |
| control | — | 1036.68 ± 30.32 | 0.00% |

Results: The number of migrated endothelial cells was significantly reduced by the action of mPEG$_2$-NHS-HM-1. Compared with the blank control group, it inhibited the migration of HUVEC induced by 5% fetal bovine serum and 1% ECGS. The inhibition of cell migration by mPEG$_2$-NHS$_{5k}$-HM-1 at 40 µg/mL and 50 µg/mL was significantly different from that of the blank control (P<0.01), and the inhibition rate reached 50.21% and 54.18%, respectively; the inhibition of cell migration by mPEG$_2$-NHS$_{10k}$-HM-1 at 60 µg/mL and 70 µg/mL was significantly different from that of the blank control (P<0.01). The inhibition rates reached 51.11% and 60.40%, respectively; the inhibition of cell migration by mPEG$_2$-NHS$_{20k}$-HM-1 at 80 µg/mL and 90 µg/mL was significantly different from that of the blank control ( P<0.01), the inhibition rates reached 50.53% and 58.07%, respectively; the inhibition of cell migration by mPEG$_2$-NHS$_{40k}$-HM-1 at 100 µg/mL and 110 µg/mL was extremely significant compared with the blank control. Sexual differences (P<0.01), the inhibition rates reached 50.13% and 55.20%, respectively.

TABLE 21 mPEG-ALD-HM-1 Inhibition of HUVEC migration

| Groups | Doses (µg/mL) | cell migration number (Mean ± SD) | inhibition rate (%) |
|---|---|---|---|
| mPEG-ALD$_{5k}$-HM-1 | 30 | 606.88 ± 58.90 | 41.02%* |
|  | 40 | 494.52 ± 52.69 | 51.94%** |
|  | 50 | 415.39 ± 44.92 | 59.63%** |
|  | 60 | 578.69 ± 66.03 | 43.76%* |
| mPEG-ALD$_{10k}$-HM-1 | 50 | 604.31 ± 52.14 | 41.27%* |
|  | 60 | 514.38 ± 42.38 | 50.01%** |
|  | 70 | 417.96 ± 50.48 | 59.38%** |
|  | 80 | 548.54 ± 56.22 | 46.69%* |
| mPEG-ALD$_{20k}$-HM-1 | 70 | 611.92 ± 52.08 | 40.53%* |
|  | 80 | 507.07 ± 40.74 | 50.72%** |
|  | 90 | 403.15 ± 48.80 | 60.82%** |
|  | 100 | 564.59 ± 50.42 | 45.13%* |
| mPEG-ALD$_{40k}$-HM-1 | 90 | 534.34 ± 56.62 | 48.07%* |
|  | 100 | 510.47 ± 60.56 | 50.39%** |
|  | 110 | 471.88 ± 46.27 | 54.14%** |
|  | 120 | 565.31 ± 50.34 | 45.06%* |
| Avastin | 10 | 532.80 ± 60.06 | 48.22%* |
| control | — | 1028.96 ± 36.42 | 0.00% |

Results: The number of migrated endothelial cells was significantly reduced by the action of mPEG-ALD-HM-1. Compared with the blank control group, it inhibited the migration of HUVEC induced by 5% fetal bovine serum and 1% ECGS. The inhibition of cell migration by mPEG-ALD$_{5k}$-HM-1 at 40 µg/mL and 50 µg/mL was significantly different from that of the blank control (P<0.01), and the inhibition rate reached 51.94. % and 59.63%; the inhibition of cell migration by mPEG-ALD$_{10k}$-HM-1 at 60 µg/mL and 70 µg/mL was significantly different from that of the blank control (P<0.01). The inhibition rates reached 50.01% and 59.38%, respectively; the inhibition of cell migration by mPEG-ALD$_{20k}$-HM-1 at 80 µg/mL and 90 µg/mL was significantly different from that of the blank control ( P<0.01), the inhibition rate reached 50.72% and 60.82%, respectively; the inhibition of cell migration by mPEG-ALD$_{40k}$-HM-1 at 100 µg/mL and 110 µg/mL was extremely significant compared with the blank control (P<0.01), the inhibition rates reached 50.39% and 54.14%, respectively.

TABLE 22 mPEG-bALD-HM-1 Inhibition of HUVEC migration

| Groups | Doses (µg/mL) | Cell Migration number (Mean ± SD) | Inhibition rate (%) |
|---|---|---|---|
| mPEG-bALD$_{5k}$-HM-1 | 30 | 654.96 ± 52.07 | 40.03%* |
|  | 40 | 545.96 ± 45.32 | 50.01%** |
|  | 50 | 489.28 ± 46.98 | 55.20%** |
|  | 60 | 577.96 ± 58.76 | 47.08%* |
| mPEG-bALD$_{10k}$-HM-1 | 50 | 589.97 ± 56.24 | 45.98%* |
|  | 60 | 483.16 ± 50.26 | 55.76%** |
|  | 70 | 432.71 ± 50.04 | 60.38%** |
|  | 80 | 581.13 ± 60.76 | 46.79%* |
| mPEG-bALD$_{10k}$-HM-1 | 70 | 614.44 ± 49.28 | 43.74%* |
|  | 80 | 484.04 ± 52.74 | 55.68%** |
|  | 90 | 504.35 ± 48.36 | 53.82%** |
|  | 100 | 568.57 ± 56.90 | 47.94%* |
| mPEG-bALD$_{40k}$-HM-1 | 90 | 652.01 ± 52.63 | 40.30%* |
|  | 100 | 523.03 ± 60.52 | 52.11%** |
|  | 110 | 545.63 ± 46.84 | 50.04%** |
|  | 120 | 596.64 ± 50.46 | 45.37%* |
| Avastin | 10 | 572.06 ± 48.92 | 47.62%* |
| control | — | 1092.14 ± 30.72 | 0.00% |

Results: Under the action of mPEG-bALD-HM-1, the number of migrated endothelial cells was significantly reduced. Compared with the blank control group, it inhibited the migration of HUVEC induced by 5% fetal bovine serum and 1% ECGS. The inhibition of cell migration by mPEG-bALD$_{5k}$-HM-1 at 40 μg/mL and 50 μg/mL was significantly different from that of the blank control (P<0.01), and the inhibition rate reached 50.01. % and 55.20%; mPEG-bALD$_{10k}$-HM-1 inhibited cell migration at 60 μg/mL and 70 μg/mL, and there was a significant difference (P<0.01) compared with the blank control. The inhibition rates reached 55.76% and 60.38%, respectively; the inhibition of cell migration by mPEG-bALD$_{20k}$-HM-1 at 80 μg/mL and 90 μg/mL was significantly different from that of the blank control ( P<0.01), the inhibition rates reached 55.68% and 53.82%, respectively; the inhibition of cell migration by mPEG-bALD$_{40k}$-HM-1 at 100 μg/mL and 110 μg/mL was significantly higher than that of the blank control. Sexual differences (P<0.01), the inhibition rates reached 52.11% and 50.04%, respectively.

Example 6: Effect of mPEG-HM-1 on the Proliferation of Mouse Spleen Lymphocytes

The spleen of the mice was taken out under aseptic conditions, washed 3 times in empty 1640 medium, ground in 5 mL syringe core, filtered through a 200-mesh sieve, and made into a single cell suspension, centrifuged (1000 rpm×5 min), and the supernatant was discarded. Tris-NH$_4$Cl was used to break the red blood cells, and the cells were allowed to stand in an ice water bath for 4 min, centrifuged (1000 rpm×5 min), the supernatant was discarded, and the cells were washed twice with sterile PBS. Finally, cells were suspended in RPMI 1640 medium (5 mL) supplemented with 10% calf serum, counted, adjusted to a cell concentration of 5×10$^6$/mL, and cultured in a 96-well culture plate The test group consisted of blank control group, concanavalin A (ConA) group, dexamethasone (Dex) group (0.02 mg/mL) and mPEG-HM-1 group. After each group was added with 100 μL/well of spleen lymphocyte suspension, the blank control group was added with 100 μL of empty 1640 medium, ConA group was added with ConA (final concentration of 5 μg/mL), Dex group was added with Dex, and the experimental group was added with different ConA to final concentration was 5 μg/mL, in addition to adding mPEG-HM-1. The cells were cultured in a 37° C. cell culture chamber for 48 h. After the completion of the culture, 20 μL of MTT was added to each well, and the culture was continued for 4 h. Finally, all the solutions in each well were discarded, 100 μL of DMSO was added to each well, and the mixture was shaken and detected by a microplate reader OD value at 570 nm, 5 parallels per hole. The results are shown in Table 23 to Table 26.

TABLE 23 mPEG-SC-HM-1Effect on mouse spleen lymphocyte proliferation

| Groups | Doses (μg/mL) | A570 nm/A630 nm | Inhibition Rate (%) |
|---|---|---|---|
| mPEG-SC$_{5k}$-HM-1 | 5 | 0.6253 ± 0.0947 | 9.32% |
|  | 10 | 0.5480 ± 0.1081 | 20.54% |
|  | 20 | 0.4954 ± 0.1219 | 28.16% |
| mPEG-SC$_{10k}$-HM-1 | 10 | 0.6234 ± 0.0976 | 9.60% |
|  | 20 | 0.5488 ± 0.1052 | 20.42% |
|  | 40 | 0.4788 ± 0.1282 | 30.57% |
| mPEG-SC$_{20k}$-HM-1 | 20 | 0.6213 ± 0.0996 | 9.91% |
|  | 40 | 0.5444 ± 0.1120 | 21.06% |
|  | 80 | 0.4741 ± 0.1270 | 31.25% |

TABLE 23-continued mPEG-SC-HM-1Effect on mouse spleen lymphocyte proliferation

| Groups | Doses (μg/mL) | A570 nm/A630 nm | Inhibition Rate (%) |
|---|---|---|---|
| mPEG-SC$_{40k}$-HM-1 | 40 | 0.6212 ± 0.0972 | 9.92% |
|  | 80 | 0.5493 ± 0.1056 | 20.34% |
|  | 160 | 0.4794 ± 0.1214 | 30.48% |
| ConA | — | 0.6896 ± 0.0249 | — |
| Dex | 20 | 0.3809 ± 0.1036 | 44.76% |
| Negative | — | 0.6082 ± 0.0398 | — |

Results: mPEG-SC-HM-1 with different molecular weight inhibited the proliferation of mouse spleen lymphocytes to some extent. The inhibition rate of mPEG-SC$_{10k}$-HM-1 at 40 μg/mL reached 30.57. %, mPEG-SC$_{20k}$-HM-1 dose at 80 μg/mL reached 31.25%, mPEG-SC$_{40k}$-HM-1 dose at 160 μg/mL reached 30.48%; and each drug group inhibition exhibits a dose-dependent relationship.

TABLE 24 mPEG$_2$-NHS-HM-1Effect on mouse spleen lymphocyte proliferation

| Groups | Doses (μg/mL) | A570 nm/A630 nm | Inhibition Rate (%) |
|---|---|---|---|
| mPEG$_2$-NHS$_{5k}$-HM-1 | 5 | 0.6304 ± 0.0983 | 8.96% |
|  | 10 | 0.5624 ± 0.1098 | 18.78% |
|  | 20 | 0.4873 ± 0.1126 | 29.62% |
| mPEG$_2$-NHS$_{10k}$-HM-1 | 10 | 0.6239 ± 0.1086 | 9.90% |
|  | 20 | 0.5533 ± 0.1067 | 20.09% |
|  | 40 | 0.4747 ± 0.1174 | 31.44% |
| mPEG$_2$-NHS$_{20k}$-HM-1 | 20 | 0.6082 ± 0.0990 | 12.16% |
|  | 40 | 0.4879 ± 0.1156 | 29.53% |
|  | 80 | 0.4375 ± 0.1095 | 36.82% |
| mPEG$_2$-NHS$_{40k}$-HM-1 | 40 | 0.6191 ± 0.0984 | 10.59% |
|  | 80 | 0.4985 ± 0.1248 | 28.01% |
|  | 160 | 0.4827 ± 0.1136 | 30.28% |
| ConA | — | 0.6924 ± 0.0292 | — |
| Dex | 20 | 0.3832 ± 0.1042 | 44.66% |
| Negative | — | 0.6140 ± 0.0362 | — |

Results: mPEG$_2$-NHS-HM-1 with different molecular weights inhibited the proliferation of mouse spleen lymphocytes to a certain extent. The inhibition rate of mPEG$_2$-NHS$_{10k}$-HM-1 at 40 μg/mL reached 31.44%, mPEG$_2$-NHS$_{20k}$-HM-1 at 80 μg/mL reached 36.82%, mPEG$_2$-NHS$_{40k}$-HM-1 at 160 μg/mL reached 30.28%; and the inhibition of each drug group showed certain dose-dependent relationship.

TABLE 25 mPEG-ALD-HM-1Effect on mouse spleen lymphocyte proliferation

| Groups | Doses (μg/mL) | A570 nm/A630 nm | Inhibition Rate (%) |
|---|---|---|---|
| mPEG-ALD$_{5k}$-HM-1 | 5 | 0.6241 ± 0.0917 | 9.14% |
|  | 10 | 0.5448 ± 0.1072 | 20.68% |
|  | 20 | 0.4779 ± 0.1178 | 30.42% |
| mPEG-ALD$_{10k}$-HM-1 | 10 | 0.6116 ± 0.1046 | 10.96% |
|  | 20 | 0.5352 ± 0.1022 | 22.08% |
|  | 40 | 0.4651 ± 0.1086 | 32.29% |
| mPEG-ALD$_{20k}$-HM-1 | 20 | 0.6035 ± 0.0989 | 12.14% |
|  | 40 | 0.4876 ± 0.1259 | 29.02% |
|  | 80 | 0.4406 ± 0.1074 | 35.85% |

TABLE 25-continued mPEG-ALD-HM-1Effect on mouse spleen lymphocyte proliferation

| Groups | Doses (μg/mL) | A570 nm/A630 nm | Inhibition Rate (%) |
|---|---|---|---|
| mPEG-ALD$_{40k}$-HM-1 | 40 | 0.6176 ± 0.0998 | 10.09% |
|  | 80 | 0.5040 ± 0.1239 | 26.63% |
|  | 160 | 0.4770 ± 0.1057 | 30.56% |
| ConA | — | 0.6869 ± 0.0294 | — |
| Dex | 20 | 0.3715 ± 0.1266 | 45.92% |
| Negative | — | 0.6298 ± 0.0442 | — |

Results: mPEG-ALD-HM-1 with different molecular weights inhibited the proliferation of mouse spleen lymphocytes to some extent. When the dose of mPEG-ALD$_{5k}$-HM-1 was 20 μg/mL, the inhibition rate reached 30.42.%, mPEG-ALD$_{10k}$-HM-1 was administered at a dose of 40 μg/mL, and the inhibition rate was 32.29%. The dose of mPEG-ALD$_{20k}$-HM-1 was 80 μg/mL, and the inhibition rate was 35.85%. The dose of mPEG-ALD$_{40k}$-HM-1 was 160 μg/mL and the inhibition rate reached 30.56%; and the inhibition of each administration group showed a dose-dependent relationship.

TABLE 26 mPEG-bALD-HM-1Effect on mouse spleen lymphocyte proliferation

| Groups | Doses (μg/mL) | A570 nm/A630 nm | InhibitionRate (%) |
|---|---|---|---|
| mPEG-bALD$_{5k}$-HM-1 | 5 | 0.6257 ± 0.1022 | 9.82% |
|  | 10 | 0.5645 ± 0.1114 | 18.64% |
|  | 20 | 0.4957 ± 0.1286 | 28.56% |
| mPEG-bALD$_{10k}$-HM-1 | 10 | 0.6179 ± 0.1049 | 10.94% |
|  | 20 | 0.5469 ± 0.1122 | 21.18% |
|  | 40 | 0.4666 ± 0.1040 | 32.75% |
| mPEG-bALD$_{20k}$-HM-1 | 20 | 0.6104 ± 0.1005 | 12.02% |
|  | 40 | 0.4988 ± 0.1173 | 28.10% |
|  | 80 | 0.4453 ± 0.1054 | 35.82% |
| mPEG-bALD$_{40k}$-HM-1 | 40 | 0.6191 ± 0.0986 | 10.77% |
|  | 80 | 0.5089 ± 0.1230 | 26.65% |
|  | 160 | 0.4848 ± 0.1146 | 30.12% |
| ConA | — | 0.6938 ± 0.0308 | — |
| Dex | 20 | 0.3905 ± 0.1094 | 43.72% |
| Negative | — | 0.6316 ± 0.0392 | — |

Results: mPEG-bALD-HM-1 with different molecular weights inhibited the proliferation of mouse spleen lymphocytes to some extent. The dose of mPEG-bALD$_{10k}$-HM-1 was 40 μg/mL, and the inhibition rate reached 32.75%. The inhibition rate of mPEG-bALD$_{20k}$-HM-1 was 35.82% at 80 μg/mL, and the inhibition rate of mPEG-bALD$_{40k}$-HM-1 was 30.12% at 160 μg/mL. and the inhibition of each administration group showed a dose-dependent relationship.

Example 7: Effect of mPEG-HM-1 on IL-1β Production by Mouse Peritoneal Macrophages (1) IL-1β production: mice were intraperitoneally injected with 1 mL of broth (containing 6%) starch, and three days later, the mouse peritoneal macrophages were aseptically taken, washed twice with 1640 medium, and the cell concentration was adjusted to 2×10$^6$ cells/mL, inject into a 24-well culture plate, 1 mL per well, incubate for 3 hours in a cell culture incubator, shake once every 30 minutes, and allow the cells to fully adhere. Then, it was washed twice with the culture solution to remove unattached cells. The blank group was added with PBS, the positive group was added with the positive drug dexamethasone (Dex), the model group was not administered, to the experimental group was added low, medium and high three concentrations of mPEG-HM-1, and the culture was continued for 48 hours after the administration, 1000 r/min. Centrifuge for 15 min. The supernatant was taken as a sample for testing activity of IL-1β.

(2) Determination of IL-1β content: using R&D mouse IL-1β enzyme-linked immunosorbent assay kit, according to the kit instructions as follows: respectively, the tested samples and different concentrations of standard products, sealed with sealing tape the reaction well and incubated at 37° C. for 90 min; the plate was washed four times; the biotinylated antibody working solution (100 μL/well) was added, and the reaction well was sealed with sealing paper, incubated at 37° c. for 60 min; the plate was washed four times; Add the enzyme conjugate working solution (100 μL/well), seal the reaction well with sealing paper, incubate at 37° C. for 30 min; wash the plate four times; add color reagent (100 μL/well), incubate at 37° C. 10-20 min, add stop solution (100 μL/well), mix and measure OD450 value. The results are shown in Tables 27 to 30.

TABLE 27 mPEG-SC-HM-1Effect on mouse peritoneal macrophages IL-1β production

| Groups | dose (μg/mL) | IL-1β (pg/mL) | Inhibition Rate (%) |
|---|---|---|---|
| mPEG-SC$_{5k}$-HM-1 | 5 | 762.83 ± 15.46** | 18.59% |
|  | 10 | 678.12 ± 12.09** | 27.63% |
|  | 20 | 561.18 ± 13.21** | 40.11% |
| mPEG-SC$_{10k}$-HM-1 | 10 | 758.05 ± 15.18** | 19.10% |
|  | 20 | 666.50 ± 11.93** | 28.87% |
|  | 40 | 553.03 ± 14.12** | 40.98% |
| mPEG-SC$_{20k}$-HM-1 | 20 | 761.42 ± 16.96** | 18.74% |
|  | 40 | 653.20 ± 18.59** | 30.29% |
|  | 80 | 512.27 ± 10.50** | 45.33% |
| mPEG-SC$_{40k}$-HM-1 | 40 | 774.07 ± 15.32** | 17.39% |
|  | 80 | 670.72 ± 16.71** | 28.42% |
|  | 160 | 553.22 ± 10.82** | 40.96% |
| Dex | 20 | 361.03 ± 18.27** | 61.47% |
| Model group | — | 937.02 ± 4.16 | — |
| Negative control | — | 9.75 ± 0.62 | — |

Results: mPEG-SC-HM-1 with different molecular weights significantly inhibited the proliferation of mouse spleen lymphocytes, and there was a significant difference compared with the negative group. When the dose of mPEG-SC$_{20k}$-HM-1 was administered at 80 μg/mL, the inhibition rate reached 45.33% and showed a dose-dependent relationship.

TABLE 28 mPEG$_2$-NHS-HM-1Effect on mouse peritoneal macrophages IL-1β production

| Groups | dose (μg/mL) | IL-1β (pg/mL) | Inhibition Rate (%) |
|---|---|---|---|
| mPEG$_2$-NHS$_{5k}$-HM-1 | 5 | 763.97 ± 15.46** | 17.51% |
|  | 10 | 681.45 ± 12.09** | 26.42% |
|  | 20 | 563.37 ± 13.21** | 39.17% |
| mPEG$_2$-NHS$_{10k}$-HM-1 | 10 | 758.32 ± 15.18** | 18.12% |
|  | 20 | 675.25 ± 11.93** | 27.09% |
|  | 40 | 546.79 ± 14.12** | 40.96% |
| mPEG$_2$-NHS$_{20k}$-HM-1 | 20 | 759.06 ± 16.96** | 18.04% |
|  | 40 | 655.24 ± 18.59** | 29.25% |
|  | 80 | 552.35 ± 10.50** | 40.36% |

TABLE 28-continued mPEG$_2$-NHS-HM-1Effect on mouse peritoneal macrophages IL-1β production

| Groups | dose (μg/mL) | IL-1β (pg/mL) | Inhibition Rate (%) |
|---|---|---|---|
| mPEG$_2$-NHS$_{40k}$-HM-1 | 40 | 756.84 ± 15.32** | 18.28% |
|  | 80 | 673.30 ± 16.71** | 27.30% |
|  | 160 | 568.00 ± 10.82** | 38.67% |
| Dex | 20 | 368.23 ± 18.27** | 60.24% |
| Model Group | — | 926.14 ± 3.98 | — |
| Negative control | — | 9.48 ± 0.59 | — |

Results: mPEG$_2$-NHS-HM-1 with different molecular weights significantly inhibited the proliferation of mouse spleen lymphocytes, and there was a significant difference compared with the negative group. when the dose of mPEG-SC$_{20k}$-HM-1 was administered at 80 μg/mL, the inhibition rate reached 45.33% and showed a dose-dependent relationship.

TABLE 29 mPEG-ALD-HM-1Effect on mouse peritoneal macrophages IL-1β production

| Groups | dose (μg/mL) | IL-1β (pg/mL) | Inhibition Rate (%) |
|---|---|---|---|
| mPEG-ALD$_{5k}$-HM-1 | 5 | 734.73 ± 16.59** | 19.87% |
|  | 10 | 654.50 ± 18.43** | 28.62% |
|  | 20 | 516.13 ± 10.95** | 43.71% |
| mPEG-ALD$_{10k}$-HM-1 | 10 | 724.09 ± 16.59** | 21.03% |
|  | 20 | 620.94 ± 18.43** | 32.28% |
|  | 40 | 455.16 ± 10.95** | 50.36% |
| mPEG-ALD$_{20k}$-HM-1 | 20 | 729.13 ± 13.12** | 20.48% |
|  | 40 | 628.18 ± 15.34** | 31.49% |
|  | 80 | 438.93 ± 12.56** | 52.13% |
| mPEG-ALD$_{40k}$-HM-1 | 40 | 742.06 ± 16.59** | 19.07% |
|  | 80 | 664.40 ± 18.43** | 27.54% |
|  | 160 | 495.96 ± 10.95** | 45.91% |
| Dex | 20 | 361.45 ± 19.17** | 60.58% |
| Model Group | — | 916.92 ± 3.09 | — |
| Negative | — | 9.06 ± 0.65 | — |

TABLE 30 mPEG-bALD-HM-1Effect on mouse peritoneal macrophages IL-1β production

| Groups | dose (μg/mL) | IL-1β (pg/mL) | Inhibition Rate (%) |
|---|---|---|---|
| mPEG-bALD$_{5k}$-HM-1 | 5 | 729.25 ± 18.34** | 20.92% |
|  | 10 | 659.63 ± 16.52** | 28.47% |
|  | 20 | 533.11 ± 10.87** | 42.19% |
| mPEG-bALD$_{10k}$-HM-1 | 10 | 720.77 ± 16.65** | 21.84% |
|  | 20 | 633.90 ± 14.73** | 31.26% |
|  | 40 | 460.53 ± 10.42** | 50.06% |
| mPEG-bALD$_{20k}$-HM-1 | 20 | 738.66 ± 12.81** | 19.90% |
|  | 40 | 640.26 ± 14.28** | 30.57% |
|  | 80 | 487.37 ± 12.06** | 47.15% |
| mPEG-bALD$_{40k}$-HM-1 | 40 | 740.78 ± 16.79** | 19.67% |
|  | 80 | 648.10 ± 14.55** | 29.72% |
|  | 160 | 518.91 ± 12.90** | 43.73% |
| Dex | 20 | 359.92 ± 19.17** | 60.97% |
| Model Group | — | 922.17 ± 4.15 | — |
| Negative | — | 9.84 ± 0.59 | — |

The results showed that mPEG-HM-1 with different molecular weights inhibited the proliferation of mouse spleen lymphocytes, and mPEG-ALD$_{10k}$-HM-1 and mPEG-bALD$_{10k}$-HM-1, at the dose of 40 μg/mL, reached the inhibition rate that is above 50%.

Example 8: Effect of mPEG-HM-1 on Xylene-Induced Ear Swelling in Mice

Kunming mice were used. The saline group was used as the blank control group, the aspirin group (200 mg/kg) as the positive control group, and the mPEG-HM-1 administration group as the experimental group. Mice were administered once daily for 5 consecutive days. The blank control group was given an equal volume of physiological saline. One hour after the last administration, 0.05 mL of xylene was applied to both sides of the right ear of the mice to cause inflammation, and the left ear was not coated as normal ears. After 2 h, the mice were sacrificed by dislocation, and the ears were cut along the auricle. Ear pieces were taken with a puncher, weighed, and the swelling degree and swelling rate were calculated. Swelling degree=right ear piece weight-left ear piece weight, swelling rate=(swelling degree/left ear piece weight)×100%. Statistical t-test was performed on the test results, *P<0.05 was a significant difference, and **P<0.01 was a very significant difference. See Table 31 to Table 34 for the results.

TABLE 31 mPEG-SC-HM-1Effect on mice ear swelling caused by p-xylene

| Groups | dosage (mg/kg) | swelling (mg) | Inhibition Rate (%) |
|---|---|---|---|
| mPEG-SC$_{5k}$-HM-1 | 5 | 5.55 ± 0.21 | 9.57% |
|  | 10 | 4.90 ± 0.35* | 20.13% |
|  | 20 | 4.17 ± 0.19** | 32.10% |
| mPEG-SC$_{10k}$-HM-1 | 10 | 5.49 ± 0.23 | 10.55% |
|  | 20 | 4.83 ± 0.32* | 21.37% |
|  | 40 | 3.98 ± 0.21** | 35.20% |
| mPEG-SC$_{20k}$-HM-1 | 20 | 5.38 ± 0.17 | 12.36% |
|  | 40 | 4.69 ± 0.79* | 23.67% |
|  | 80 | 3.77 ± 0.33** | 38.58% |
| mPEG-SC$_{40k}$-HM-1 | 40 | 5.51 ± 0.13 | 10.27% |
|  | 80 | 4.76 ± 0.72* | 22.42% |
|  | 160 | 3.87 ± 0.27** | 37.01% |
| Aspirin | 200 | 3.07 ± 0.31** | 50.02% |
| control | — | 6.14 ± 0.29 | — |

Results: mPEG-SC-HM-1 with different molecular weights inhibited the swelling of mouse ear induced by xylene. The inhibition rate of mPEG-SC$_{5k}$-HM-1 was 32.10% when the dose was 20 mg/kg. When mPEG-SC$_{10k}$-HM-1 was administered at a dose of 40 mg/kg, the inhibition rate reached 35.20%, and when the dose of mPEG-SC$_{20k}$-HM-1 was 80 mg/kg, the inhibition rate reached 38.58%. When mPEG-SC$_{40k}$-HM-1 was administered at a dose of 160 mg/kg, the inhibition rate reached 37.01%, and showed a dose-dependent relationship.

TABLE 32 mPEG$_2$-NHS-HM-1Effect on mice ear swelling caused by p-xylene

| Groups | dosage (mg/kg) | swelling (mg) | Inhibition Rate (%) |
|---|---|---|---|
| mPEG$_2$-NHS$_{5k}$-HM-1 | 5 | 5.56 ± 0.19 | 10.02% |
|  | 10 | 4.94 ± 0.28* | 20.05% |
|  | 20 | 4.31 ± 0.20** | 30.23% |
| mPEG$_2$-NHS$_{10k}$-HM-1 | 10 | 5.39 ± 0.14 | 12.76% |
|  | 20 | 4.72 ± 0.72* | 23.57% |
|  | 40 | 4.13 ± 0.35** | 33.19% |
| mPEG$_2$-NHS$_{20k}$-HM-1 | 20 | 5.52 ± 0.16 | 10.65% |
|  | 40 | 4.80 ± 0.29* | 22.37% |
|  | 80 | 3.96 ± 0.22** | 35.92% |

TABLE 32-continued mPEG$_2$-NHS-HM-1Effect on mice ear swelling caused by p-xylene

| Groups | dosage (mg/kg) | swelling (mg) | Inhibition Rate (%) |
|---|---|---|---|
| mPEG$_2$-NHS$_{40k}$-HM-1 | 40 | 5.47 ± 0.12 | 11.52% |
| | 80 | 4.83 ± 0.67* | 21.88% |
| | 160 | 4.19 ± 0.34** | 32.26% |
| Aspirin | 200 | 3.02 ± 0.41** | 51.11% |
| control | — | 6.18 ± 0.51 | |

Results: mPEG$_2$-NHS-HM-1 with different molecular weights inhibited the swelling of mouse ear induced by xylene. The inhibition rate of mPEG$_2$-NHS$_{5k}$-HM-1 was 30.23% when the dosage was 20 mg/kg. The inhibition rate of mPEG$_2$-NHS$_{10k}$-HM-1 was 33.19% when the dose was 40 mg/kg, and the inhibition rate was 35.92% when mPEG$_2$-NHS$_{20k}$-HM-1 was administered at 80 mg/kg. At a dose of 160 mg/kg the inhibition rate of mPEG$_2$-NHS$_{40k}$-HM-1 reached 32.26% and showed a dose-dependent relationship.

TABLE 33 mPEG-ALD-HM-1Effect on mice ear swelling caused by p-xylene

| Groups | dosage (mg/kg) | swelling (mg) | Inhibition Rate (%) |
|---|---|---|---|
| mPEG-ALD$_{5k}$-HM-1 | 5 | 5.50 ± 0.21 | 10.17% |
| | 10 | 4.80 ± 0.35* | 21.52% |
| | 20 | 4.16 ± 0.14** | 32.10% |
| mPEG-ALD$_{10k}$-HM-1 | 10 | 5.36 ± 0.12 | 12.36% |
| | 20 | 4.67 ± 0.79* | 23.67% |
| | 40 | 3.58 ± 0.33** | 41.58% |
| mPEG-ALD$_{20k}$-HM-1 | 20 | 4.89 ± 0.20 | 20.10% |
| | 40 | 4.52 ± 0.32* | 26.19% |
| | 80 | 3.70 ± 0.20** | 39.47% |
| mPEG-ALD$_{40k}$-HM-1 | 40 | 5.41 ± 0.16 | 11.53% |
| | 80 | 4.77 ± 0.62* | 22.02% |
| | 160 | 4.16 ± 0.25** | 32.09% |
| Aspirin | 200 | 3.01 ± 0.53** | 50.87% |
| control | — | 6.12 ± 0.43 | |

Results: mPEG-ALD-HM-1 with different molecular weights inhibited the swelling of mouse ear induced by xylene. The inhibition rate of mPEG-ALD$_{5k}$-HM-1 reached 32.10% at a dosage of 20 mg/kg; the inhibition rate reached 41.58% when the dose of mPEG-ALD$_{10k}$-HM-1 was 40 mg/kg, and the inhibition rate reached 39.47% when the dose of mPEG-ALD$_{20k}$-HM-1 was 80 mg/kg. The inhibition rate of mPEG-ALD$_{40k}$-HM-1 administered at a dose of 160 mg/kg reached 32.09% and showed a dose-dependent relationship.

TABLE 34 mPEG-bALD-HM-1Effect on mice ear swelling caused by p-xylene

| Groups | dosage (mg/kg) | swelling (mg) | Inhibition Rate (%) |
|---|---|---|---|
| mPEG-bALD$_{5k}$-HM-1 | 5 | 5.44 ± 0.19 | 10.36% |
| | 10 | 4.83 ± 0.30* | 20.47% |
| | 20 | 4.18 ± 0.25** | 31.08% |
| mPEG-bALD$_{10k}$-HM-1 | 10 | 5.37 ± 0.14 | 11.54% |
| | 20 | 4.64 ± 0.72* | 23.63% |
| | 40 | 3.59 ± 0.35** | 40.88% |
| mPEG-bALD$_{20k}$-HM-1 | 20 | 5.03 ± 0.18 | 17.13% |
| | 40 | 4.64 ± 0.34* | 23.62% |
| | 80 | 3.78 ± 0.27** | 37.76% |
| mPEG-bALD$_{40k}$-HM-1 | 40 | 5.25 ± 0.12 | 13.45% |
| | 80 | 4.68 ± 0.72* | 22.94% |
| | 160 | 4.06 ± 0.26** | 33.09% |
| Aspirin | 200 | 2.98 ± 0.53** | 50.93% |
| control | — | 6.07 ± 0.32 | |

Results: mPEG-bALD-HM-1 with different molecular weights significantly inhibited the swelling of mouse ear caused by xylene. When the dose of mPEG-bALD$_{5k}$-HM-1 was 20 mg/kg, the inhibition rate reached 31.08%, when the dose of mPEG-bALD$_{10k}$-HM-1 was 40 mg/kg, the inhibition rate reached 40.88%, When the dose of mPEG-ALD$_{20k}$-HM-1 was 80 mg/kg, the inhibition rate reached 37.76%, and when the dose of mPEG-bALD$_{40k}$-HM-1 was 160 mg/kg, the inhibition rate reached 33.09%, and showed a dose-dependent relationship.

Example 9: Immunoprotective Effect of mPEG-HM-1 on Collagen-Induced Mouse Arthritis Animal Model A collagen mouse arthritis animal model was constructed to study the therapeutic effect of mPEG-HM-1 on collagen induced arthritis (CIA) in mice. Mice were used as testing animals, SPF grade DBA/1 mice, males, 7-8 weeks old, weighing 18-22 g, were randomly divided into normal control group, model control group, mPEG-HM-1 group, and positive drug control group (methotrexate 1 mg/kg). On the 0th day, except for the normal group, the mouse CIA model was established by the method of dissolving chicken cartilage type III collagen (cIII) into a 4 mg/mL solution with 0.1 mol/L acetic acid and leave overnight at 4° C. in a refrigerator. On the day of the experiment, type III collagen was fully emulsified with a full Freund's adjuvant (CFA) containing 4 mg/mL Myeobaeterium tuberculosis strain H37Rv. After anesthetizing the DBA/1 mice, 50 uL emulsifier was injected into the tail skin to sensitize the mouse. After 21 days, 4 mg/mL of type III collagen (cIII) and equal volume incomplete Freund's adjuvant (IFA) were fully emulsified, and the mice were re-immunized with the same dose of emulsifier at the tail. Subcutaneous injection from the 30th day of modeling: mPEG-HM-1 group: once every three days; positive drug control group (methotrexate 1 mg/kg): once every 5 days, 3 times in a row; normal control group and Model control group (saline): 10 consecutive days. The body weight and joint score were measured every 3 days from the 21st day to the 70th day after modeling, and the diameters of the left, right hind foot ankle were measured to observe the effect of the drug on collagen-induced arthritis in mice. On the 70th day, the mice were euthanized by dislocation.

The evaluation indexes of arthritis are as follows: (1) Joint score: limbs: scored on 0-4 level with five grades: 0=no erythema or redness; 1=slight erythema or swelling, one of which has erythema or swelling of the anterior/posterior joint; 2=more than one toe with erythema or swelling; 3=swelling of the feet under the ankle or wrist; 4=swelling of all the feet including the ankle. The four feet of the mice were scored separately, with a maximum score of 16 points. Joint scoring was performed every 3 days before modeling, and day 21 to day 70 after modeling, and the results were recorded. (2) Measuring diameter of the ankles: the diameters from inside to outside of the ankles of the left and right ankles of the mice, and thickness of the feet, were measured by vernier calipers before modeling and every three days between the 21st to 70th days after the modeling, and the results were recorded.

The test was repeated 3 times independently. The results obtained by the test were expressed as mean±SD, and a statistical T test was performed. *P<0.05 was considered as a significant difference, and **P<0.01 was a very significant difference.

TABLE 35 mPEG-SC-HM-1Immunoprotective effect on collagen-induced mouse arthritis animal model

| Group | Group size | Doses (mg/kg) | Left and right paw swelling (mm) | Joint swelling (mm) | Clinical score |
|---|---|---|---|---|---|
| Normal control group | 10 | — | 0.18 ± 0.07 | 0.16 ± 0.05 | 0.00 ± 0.00 |
| Model control group | 10 | — | 2.29 ± 0.39 | 2.00 ± 0.47 | 15.65 ± 1.90 |
| Positive control group | 10 | 1 | 0.70 ± 0.12** | 0.73 ± 0.12** | 8.32 ± 1.35** |
| mPEG-SC$_{5k}$-HM-1 | 10 | 10 | 0.79 ± 0.11** | 0.81 ± 0.12** | 9.10 ± 1.27** |
| mPEG-SC$_{10k}$-HM-1 | 10 | 20 | 0.77 ± 0.12** | 0.79 ± 0.13** | 9.06 ± 1.24** |
| mPEG-SC$_{20k}$-HM-1 | 10 | 40 | 0.72 ± 0.15** | 0.76 ± 0.12** | 9.00 ± 1.25** |
| mPEG-SC$_{40k}$-HM-1 | 10 | 80 | 0.80 ± 0.16** | 0.80 ± 0.16** | 9.09 ± 1.33** |

Results: Compared with normal mice, mice tails were injected intradermally with inactivated *M. tuberculosis* complete Freund's adjuvant and collagen in an equal volume of emulsifier. After 21 days, the tail was injected intradermally mixed with emulsifier of incomplete Freund's adjuvant and equal volume collagen in the left, on the 27th day after immunization, the paws of CIA mice were swollen, and the index of arthritis index was increased. In the model group the swelling peaks on the 45th to 60th day. At 35 days, the weight in the model group did not increase at all, and there was a slight decrease in the later period. mPEG-SC-HM-1 of different molecular weights exerted immunoprotective effects in collagen-induced mouse arthritis animal models. The positive control group and mPEG-SC-HM-1 group have extremely significant differences compared with the model group. (p**<0.01); the limbs score of mPEG-SC$_{20k}$-HM-1 group was significantly lower than that of the model control group, and the protective effect was the most significant.

TABLE 36 mPEG$_2$-NHS-HM-1Immunoprotective effect on collagen-induced mouse arthritis animal model

| Group | Group size | Doses (mg/kg) | Left and right paw swelling (mm) | Joint swelling (mm) | Clinical score |
|---|---|---|---|---|---|
| Normal control group | 10 | — | 0.17 ± 0.08 | 0.15 ± 0.06 | 0.00 ± 0.00 |
| Model control group | 10 | — | 2.23 ± 0.35 | 2.05 ± 0.42 | 15.78 ± 1.87 |
| Positive control group | 10 | 1 | 0.71 ± 0.13** | 0.72 ± 0.13** | 8.41 ± 1.25** |
| mPEG$_2$-NHS$_{5k}$-HM-1 | 10 | 10 | 0.76 ± 0.11** | 0.78 ± 0.12** | 9.01 ± 1.28** |
| mPEG$_2$-NHS$_{10k}$-HM-1 | 10 | 20 | 0.74 ± 0.14** | 0.75 ± 0.15** | 8.83 ± 1.32** |
| mPEG$_2$-NHS$_{20k}$-HM-1 | 10 | 40 | 0.75 ± 0.12** | 0.72 ± 0.16** | 8.67 ± 1.35** |
| mPEG$_2$-NHS$_{40k}$-HM-1 | 10 | 80 | 0.79 ± 0.15** | 0.76 ± 0.14** | 8.98 ± 1.30** |

Results: Compared with normal mice, mice tails were injected intradermally with inactivated *M. tuberculosis* complete Freund's adjuvant and collagen in an equal volume of emulsifier. After 21 days, the tail was injected intradermally mixed with emulsifier of incomplete Freund's adjuvant and equal volume collagen in the left, on the 27th day after immunization, the paws of CIA mice were swollen, and the index of arthritis index was increased. In the model group the swelling peaks on the 45th to 60th day. At 35 days, the weight in the model group did not increase at all, and there was a slight decrease in the later period. mPEG$_2$-NHS-HM-1 of different molecular weights exerted immunoprotective effects in collagen-induced mouse arthritis animal models. The positive control group and mPEG$_2$-NHS-HM-1 group have extremely significant differences compared with the model group. (p**<0.01); the limbs score of mPEG$_2$-NHS$_{20k}$-HM-1 group was significantly lower than that of the model control group, and the protective effect was the most significant.

TABLE 37 mPEG-ALD-HM-1 Immunoprotective effect on collagen-induced mouse arthritis animal model

| Group | Group size | Doses (mg/kg) | Left and right paw swelling (mm) | Joint swelling (mm) | Clinical score |
|---|---|---|---|---|---|
| Normal control group | 10 | — | 0.15 ± 0.06 | 0.14 ± 0.06 | 0.00 ± 0.00 |
| Model control group | 10 | — | 2.19 ± 0.32 | 1.98 ± 0.45 | 15.45 ± 1.86 |
| Positive control group | 10 | 1 | 0.68 ± 0.14** | 0.67 ± 0.13** | 8.21 ± 1.42** |
| mPEG-ALD$_{5k}$-HM-1 | 10 | 10 | 0.72 ± 0.15** | 0.74 ± 0.14** | 8.93 ± 1.27** |
| mPEG-ALD$_{10k}$-HM-1 | 10 | 20 | 0.70 ± 0.14** | 0.73 ± 0.15** | 8.65 ± 1.33** |
| mPEG-ALD$_{20k}$-HM-1 | 10 | 40 | 0.74 ± 0.13** | 0.72 ± 0.16** | 8.66 ± 1.38** |
| mPEG-ALD$_{40k}$-HM-1 | 10 | 80 | 0.79 ± 0.12** | 0.77 ± 0.14** | 8.97 ± 1.42** |

Results: Compared with normal mice, mice tails were injected intradermally with inactivated *M. tuberculosis* complete Freund's adjuvant and collagen in an equal volume of emulsifier. After 21 days, the tail was injected intradermally mixed with emulsifier of incomplete Freund's adjuvant and equal volume collagen in the left, on the 27th day after immunization, the paws of CIA mice were swollen, and the index of arthritis index was increased. In the model group the swelling peaks on the 45th to 60th day. At 35 days, the weight in the model group did not increase at all, and there was a slight decrease in the later period. mPEG-ALD-HM-1 of different molecular weights exerted immunoprotective effects in collagen-induced mouse arthritis animal models. The positive control group and mPEG-ALD-HM-1 group have extremely significant differences compared with the model group. (p**<0.01); the limbs score of mPEG-ALD$_{10k}$-HM-1 group was significantly lower than that of the model control group, and the protective effect was the most significant.

TABLE 38 mPEG-bALD-HM-1 Immunoprotective effect on collagen-induced mouse arthritis animal model

| Group | Group size | Doses (mg/kg) | Left and right paw swelling (mm) | Joint swelling (mm) | Clinical score |
|---|---|---|---|---|---|
| Normal control group | 10 | — | 0.17 ± 0.05 | 0.15 ± 0.07 | 0.00 ± 0.00 |
| Model control group | 10 | — | 2.21 ± 0.35 | 1.99 ± 0.42 | 15.36 ± 1.83 |
| Positive control group | 10 | 1 | 0.69 ± 0.15** | 0.68 ± 0.12** | 8.23 ± 1.47** |
| mPEG-bALD$_{5k}$-HM-1 | 10 | 10 | 0.74 ± 0.13** | 0.73 ± 0.15** | 8.98 ± 1.25** |
| mPEG-bALD$_{10k}$-HM-1 | 10 | 20 | 0.71 ± 0.12** | 0.74 ± 0.12** | 8.69 ± 1.38** |
| mPEG-bALD$_{20k}$-HM-1 | 10 | 40 | 0.75 ± 0.11** | 0.73 ± 0.15** | 8.67 ± 1.32** |
| mPEG-bALD$_{40k}$-HM-1 | 10 | 80 | 0.79 ± 0.13** | 0.78 ± 0.16** | 9.01 ± 1.45 ** |

Results: Compared with normal mice, mice tails were injected intradermally with inactivated *M. tuberculosis* complete Freund's adjuvant and collagen in an equal volume of emulsifier. After 21 days, the tail was injected intradermally mixed with emulsifier of incomplete Freund's adjuvant and equal volume collagen in the left, on the 27th day after immunization, the paws of CIA mice were swollen, and the index of arthritis index was increased. In the model group the swelling peaks on the 45th to 60th day. At 35 days, the weight in the model group did not increase at all, and there was a slight decrease in the later period. mPEG-bALD-HM-1 of different molecular weights exerted immunoprotective effects in collagen-induced mouse arthritis animal models. The positive control group and mPEG-bALD-HM-1 group have extremely significant differences compared with the model group. (p**<0.01); the limbs score of mPEG-bALD$_{10k}$-HM-1 group was significantly lower than that of the model control group, and the protective effect was the most significant.

Example 10: In Vivo Immunoprotective Effect of mPEG-HM-1 on Adjuvant Arthritis Rat Model An adjuvant arthritis rat model of arthritis was constructed to study the therapeutic effect of mPEG-HM-1 on adjuvant arthritis (AA) rats. Rats were used as test animals, SPF grade SD rats, males, weighing 140-160 g, were randomly divided into normal control group, model control group, mPEG-HM-1 group and positive drug control group (methotrexate 1 mg/kg). Except for the normal group, in all the rats in the test groups the adjuvant arthritis model were established on the 0th day by injecting the inactivated *Mycobacterium tuberculosis* (H37RA, 10 mg/mL) and Complete Freund's adjuvant (0.08 mL) in the left hind paw of the rat. 10 days after establishing the model, subcutaneous injections were started: mPEG-HM-1: once every three days; positive drug control group (methotrexate 1 mg/kg): once every five days, three times in a row; normal control group and Model control group (saline): 10 consecutive days. On the 8th, 11th, 14th, 17th, 20th, 23th and 26th day after modeling, the joints were scored, and the diameters of the left hind foot ankle and right hind foot ankle were examined to observe the effect of the drug on adjuvant arthritis in rats.

The evaluation indexes of arthritis are as follows: (1) Joint scores of limbs: scored on 0-4 level with five grades: 0=no erythema or redness; 1=slight erythema or swelling, one of which has erythema or swelling of the anterior/posterior joint; 2=more than one toe with erythema or swelling; 3=swelling of the feet under the ankle or wrist; 4=swelling of all the feet including the ankle. The four feet of the rats were scored separately, with a maximum score of 16 points. Joint scores were taken at 8, 11, 14, 17, 20, 23, and 26 days after modeling, and the results were recorded. (2) Measuring diameter of the ankles: the diameters from inside to outside of the left and right ankles of the rat, and thickness of the feet, were measured by vernier calipers before modeling and 8, 11, 14, 17, 20, 23 and 26 days after the modeling, and the results were recorded. The test was repeated 3 times independently. The results obtained by the test were expressed as mean±SD, and a statistical T test was performed. *P<0.05 was considered as a significant difference, and **P<0.01 was a very significant difference.

TABLE 39 mPEG-SC-HM-1 Immunoprotective effect in adjuvant arthritis rat arthritis animal models

| Group | Group size | Doses (mg/kg) | Left and right paw swelling (mm) | Joint swelling (mm) | Clinical score |
|---|---|---|---|---|---|
| Normal control group | 10 | — | 0.93 ± 0.14 | 0.30 ± 0.15 | 0.00 ± 0.00 |
| Model control group | 10 | — | 6.98 ± 1.27 | 3.74 ± 0.72 | 13.86 ± 1.65 |
| Positive control group | 10 | 1 | 3.26 ± 0.45** | 0.63 ± 0.13** | 5.04 ± 1.19** |
| mPEG-SC$_{5k}$-HM-1 | 10 | 10 | 3.96 ± 0.71** | 0.74 ± 0.18** | 5.95 ± 1.07** |
| mPEG-SC$_{10k}$-HM-1 | 10 | 20 | 3.81 ± 0.71** | 0.70 ± 0.18** | 5.52 ± 1.07** |
| mPEG-SC$_{20k}$-HM-1 | 10 | 40 | 3.75 ± 0.67** | 0.81 ± 0.20** | 5.83 ± 1.01** |
| mPEG-SC$_{40k}$-HM-1 | 10 | 80 | 3.83 ± 0.62** | 0.71 ± 0.11** | 5.88 ± 1.08** |

Results: After the model was established, the modeling rats, with the left hind paw injected with the inactivated *M. tuberculosis* complete Freund's adjuvant, rapidly developed primary arthritis in the left hind paw. Significant swelling and ulceration occurred; secondary arthritis began to appear in the right hind paw about 10 days later, the value of the score gradually increased; at the same time, the ear vascular hyperplasia was obvious, redness and swelling were obvious; the tail joint showed swelling, compared with the model group, the mPEG-SC-HM-1 group with different molecular weight can exert certain in vivo immune protection effects on the adjuvant arthritis animal model, and mPEG-SC$_{10k}$-HM-1 has the most significant effect.

TABLE 40 mPEG$_2$-NHS-HM-1 Immunoprotective effect in adjuvant arthritis rat arthritis animal models

| Group | Group size | Doses (mg/kg) | Left and right paw swelling (mm) | Joint swelling (mm) | Clinical score |
|---|---|---|---|---|---|
| Normal control group | 10 | — | 0.90 ± 0.13 | 0.31 ± 0.14 | 0.00 ± 0.00 |
| Model control group | 10 | — | 6.96 ± 1.24 | 3.72 ± 0.71 | 13.94 ± 1.62 |
| Positive control group | 10 | 1 | 3.22 ± 0.43** | 0.62 ± 0.15** | 5.02 ± 1.17** |
| mPEG$_2$-NHS$_{5k}$-HM-1 | 10 | 10 | 3.91 ± 0.73** | 0.73 ± 0.16** | 5.92 ± 1.04** |
| mPEG$_2$-NHS$_{10k}$-HM-1 | 10 | 20 | 3.80 ± 0.73** | 0.69 ± 0.19** | 5.53 ± 1.09** |
| mPEG$_2$-NHS$_{20k}$-HM-1 | 10 | 40 | 3.77 ± 0.66** | 0.80 ± 0.21** | 5.82 ± 1.03** |
| mPEG$_2$-NHS$_{40k}$-HM-1 | 10 | 80 | 3.81 ± 0.63** | 0.73 ± 0.14** | 5.89 ± 1.07** |

Results: After the model was established, the modeling rats, with the left hind paw injected with the inactivated *M. tuberculosis* complete Freund's adjuvant, rapidly developed primary arthritis in the left hind paw. Significant swelling and ulceration occurred; secondary arthritis began to appear in the right hind paw about 10 days later, the value of the score gradually increased; at the same time, the ear vascular hyperplasia was obvious, redness and swelling were obvious; the tail joint showed swelling, compared with the model group, the mPEG$_2$-NHS-HM-1 group with different molecular weight can exert certain in vivo immune protection effects on the adjuvant arthritis animal model, and mPEG$_2$-NHS$_{10k}$-HM-1 has the most significant effect.

TABLE 41 mPEG-ALD-HM-1 Immunoprotective effect in adjuvant arthritis rat arthritis animal models

| Group | Group size | Doses (mg/kg) | Left and right paw swelling (mm) | Joint swelling (mm) | Clinical score |
|---|---|---|---|---|---|
| Normal control group | 10 | — | 0.91 ± 0.15 | 0.33 ± 0.14 | 0.00 ± 0.00 |
| Model control group | 10 | — | 7.03 ± 1.21 | 3.72 ± 0.65 | 13.45 ± 1.49 |
| Positive control group | 10 | 1 | 3.21 ± 0.42** | 0.61 ± 0.14** | 5.03 ± 1.16** |
| mPEG-ALD$_{5k}$-HM-1 | 10 | 10 | 3.92 ± 0.67** | 0.72 ± 0.17** | 5.91 ± 1.09** |
| mPEG-ALD$_{10k}$-HM-1 | 10 | 20 | 3.72 ± 0.54** | 0.68 ± 0.15** | 5.39 ± 1.10** |
| mPEG-ALD$_{20k}$-HM-1 | 10 | 40 | 3.77 ± 0.62** | 0.76 ± 0.21** | 5.67 ± 1.08** |
| mPEG-ALD$_{40k}$-HM-1 | 10 | 80 | 3.80 ± 0.65** | 0.73 ± 0.17** | 5.76 ± 1.03** |

Results: After the model was established, the modeling rats, with the left hind paw injected with the inactivated *M. tuberculosis* complete Freund's adjuvant, rapidly developed primary arthritis in the left hind paw. Significant swelling and ulceration occurred; secondary arthritis began to appear in the right hind paw about 10 days later, the value of the score gradually increased; at the same time, the ear vascular hyperplasia was obvious, redness and swelling were obvious; the tail joint showed swelling, compared with the model group, the mPEG-ALD-HM-1 group with different molecular weight can exert certain in vivo immune protection effects on the adjuvant arthritis animal model, and mPEG-ALD$_{10k}$-HM-1 has the most significant effect.

TABLE 42 mPEG-bALD-HM-1 Immunoprotective effect in adjuvant arthritis rat arthritis animal models

| Group | Group size | Doses (mg/kg) | Left and right paw swelling (mm) | Joint swelling (mm) | Clinical score |
|---|---|---|---|---|---|
| Normal control group | 10 | — | 0.95 ± 0.13 | 0.32 ± 0.15 | 0.00 ± 0.00 |
| Model control group | 10 | — | 7.06 ± 1.23 | 3.75 ± 0.67 | 13.47 ± 1.42 |
| Positive control group | 10 | 1 | 3.23 ± 0.43** | 0.64 ± 0.12** | 5.04 ± 1.13** |
| mPEG-bALD$_{5k}$-HM-1 | 10 | 10 | 3.94 ± 0.65** | 0.73 ± 0.18** | 5.92 ± 1.11** |
| mPEG-bALD$_{10k}$-HM-1 | 10 | 20 | 3.73 ± 0.52** | 0.69 ± 0.13** | 5.40 ± 1.09** |
| mPEG-bALD$_{20k}$-HM-1 | 10 | 40 | 3.78 ± 0.63** | 0.77 ± 0.23** | 5.68 ± 1.10** |
| mPEG-bALD$_{40k}$-HM-1 | 10 | 80 | 3.81 ± 0.62** | 0.74 ± 0.18** | 5.78 ± 1.05** |

Results: After the model was established, the modeling rats, with the left hind paw injected with the inactivated *M. tuberculosis* complete Freund's adjuvant, rapidly developed primary arthritis in the left hind paw. Significant swelling and ulceration occurred; secondary arthritis began to appear in the right hind paw about 10 days later, the value of the score gradually increased; at the same time, the ear vascular hyperplasia was obvious, redness and swelling were obvious; the tail joint showed swelling, compared with the model group, the mPEG-bALD-HM-1 group with different molecular weight can exert certain in vivo immune protection effects on the adjuvant arthritis animal model, and mPEG-bALD$_{10k}$-HM-1 has the most significant effect.

Example 11: Effect of mPEG-HM-1 on Carrageenan-Induced Acute Inflammation of Toe Swelling in Rats SD rats were divided into blank model group, dexamethasone-positive group (5 mg/kg) and mPEG-HM-1 test group. The drug was administered once a day, and the model group was given the same volume of normal saline for 3 days and fed normally. At the first hour after the last administration, 0.1 mL of 1% carrageenan was injected subcutaneously into the right hind paw of the rats to induce inflammation. The volume of the foot was measured at 1 h, 3 h, 5 h, and 7 h after inflammation. The degree of swelling of the foot was calculated according to the following formula: the degree of swelling of the foot (mL)=the volume of the foot after inflammation−the volume before inflammation. Record the number of milliliters of spilled liquid (method: use the ballpoint pen to circle as the measurement mark at the protruding point of the right joint, and then put the right hind foot of each mouse into the volume measuring device, so that the hind limb is exposed outside the cylinder, and the depth of the immersion was determined by coinciding the circle with the liquid surface. After the foot enters the liquid, the liquid level rises, and the volume of the overflow liquid is the volume of the right hind foot of the rat, and the normal volume of the right hind foot of each mouse is sequentially determined).

TABLE 43 mPEG-SC-HM-1 Effect on carrageenan-induced acute inflammation of rat toe swelling

| group | dose (mg/kg) | Swelling (mg) | | | |
|---|---|---|---|---|---|
| | | 1 h | 3 h | 5 h | 7 h |
| mPEG-SC$_{5k}$-HM-1 | 10 | 0.24 ± 0.12 | 0.37 ± 0.14 | 0.42 ± 0.16 | 0.32 ± 0.13* |
| | 20 | 0.23 ± 0.10* | 0.33 ± 0.20 | 0.38 ± 0.13** | 0.34 ± 0.15* |
| mPEG-SC$_{10k}$-HM-1 | 20 | 0.25 ± 0.11 | 0.38 ± 0.15 | 0.43 ± 0.17 | 0.31 ± 0.11* |
| | 40 | 0.22 ± 0.09* | 0.32 ± 0.19 | 0.37 ± 0.12** | 0.34 ± 0.13* |
| mPEG-SC$_{20k}$-HM-1 | 40 | 0.28 ± 0.14* | 0.35 ± 0.17 | 0.42 ± 0.15* | 0.37 ± 0.16* |
| | 80 | 0.26 ± 0.10* | 0.33 ± 0.12 | 0.40 ± 0.13* | 0.32 ± 0.17* |
| mPEG-SC$_{40k}$-HM-1 | 80 | 0.25 ± 0.13* | 0.34 ± 0.12 | 0.44 ± 0.15* | 0.34 ± 0.16* |
| | 160 | 0.24 ± 0.12* | 0.33 ± 0.13 | 0.43 ± 0.12* | 0.33 ± 0.13* |
| Dex | 10 | 0.21 ± 0.10** | 0.25 ± 0.11** | 0.28 ± 0.11** | 0.24 ± 0.08* |
| control | — | 0.25 ± 0.18 | 0.43 ± 0.19 | 0.55 ± 0.05 | 0.36 ± 0.20 |

Results: The toes of the rats in each group were swollen rapidly after modeling. The swelling peak was reached at about 3~5 h and disappeared at 7 h. The mPEG-SC-HM-1 group with different molecular weights could significantly inhibit the rat toe swelling induced by carrageenan, and the high dose group was better than the low dose group, of which mPEG-SC$_{20k}$-HM-1 at the dose of 80 mg/kg was most effective.

TABLE 44 mPEG2-NHS-HM-1 Effect on carrageenan-induced acute inflammation of rat toe swelling

| group | dose (mg/kg) | Swelling (mg) | | | |
|---|---|---|---|---|---|
| | | 1 h | 3 h | 5 h | 7 h |
| mPEG$_2$-NHS$_{5k}$-HM-1 | 10 | 0.25 ± 0.13 | 0.36 ± 0.12 | 0.43 ± 0.17 | 0.31 ± 0.15* |
| | 20 | 0.22 ± 0.11* | 0.32 ± 0.21 | 0.36 ± 0.12** | 0.32 ± 0.16* |
| mPEG$_2$-NHS$_{10k}$-HM-1 | 20 | 0.24 ± 0.12 | 0.37 ± 0.16 | 0.42 ± 0.16 | 0.30 ± 0.12* |
| | 40 | 0.21 ± 0.10* | 0.31 ± 0.15 | 0.35 ± 0.11** | 0.33 ± 0.15* |
| mPEG$_2$-NHS$_{20k}$-HM-1 | 40 | 0.26 ± 0.15* | 0.34 ± 0.14 | 0.43 ± 0.17* | 0.36 ± 0.12* |
| | 80 | 0.25 ± 0.11* | 0.32 ± 0.13 | 0.41 ± 0.11* | 0.34 ± 0.14* |
| mPEG$_2$-NHS$_{40k}$-HM-1 | 80 | 0.26 ± 0.12* | 0.32 ± 0.11 | 0.42 ± 0.14* | 0.35 ± 0.17* |
| | 160 | 0.27 ± 0.10* | 0.35 ± 0.18 | 0.41 ± 0.13* | 0.34 ± 0.19* |
| Dex | 10 | 0.22 ± 0.11** | 0.26 ± 0.10** | 0.29 ± 0.12** | 0.25 ± 0.09* |
| Control | — | 0.24 ± 0.16 | 0.44 ± 0.17 | 0.53 ± 0.09 | 0.35 ± 0.21 |

Results: The toes of the rats in each group were swollen rapidly after modeling. The swelling peak was reached at about 3~5 h and disappeared at 7 h. The mPEG$_2$-NHS-HM-1 group with different molecular weights could significantly inhibit the rat toe swelling induced by carrageenan, and the high dose group was better than the low dose group, of which mPEG$_2$-NHS$_{10k}$-HM-1 at the dose of 40 mg/kg was most effective.

TABLE 45 mPEG-ALD-HM-1Effect on carrageenan-induced acute inflammation of rat toe swelling

| group | dose (mg/kg) | Swelling (mg) | | | |
|---|---|---|---|---|---|
| | | 1 h | 3 h | 5 h | 7 h |
| mPEG-ALD$_{5k}$-HM-1 | 10 | 0.22 ± 0.10 | 0.35 ± 0.13 | 0.41 ± 0.15 | 0.31 ± 0.12* |
| | 20 | 0.21 ± 0.11* | 0.34 ± 0.19 | 0.37 ± 0.11** | 0.35 ± 0.13* |
| mPEG-ALD$_{10k}$-HM-1 | 20 | 0.24 ± 0.12 | 0.36 ± 0.13 | 0.42 ± 0.15 | 0.32 ± 0.10* |
| | 40 | 0.21 ± 0.10* | 0.31 ± 0.20 | 0.36 ± 0.13** | 0.33 ± 0.12* |
| mPEG-ALD$_{20k}$-HM-1 | 40 | 0.27 ± 0.13* | 0.34 ± 0.16 | 0.41 ± 0.14* | 0.35 ± 0.13* |
| | 80 | 0.25 ± 0.09* | 0.32 ± 0.11 | 0.40 ± 0.15* | 0.32 ± 0.16* |
| mPEG-ALD$_{40k}$-HM-1 | 80 | 0.26 ± 0.14* | 0.35 ± 0.13 | 0.43 ± 0.14* | 0.33 ± 0.17* |
| | 160 | 0.24 ± 0.13* | 0.34 ± 0.14 | 0.44 ± 0.15* | 0.34 ± 0.15* |
| Dex | 10 | 0.22 ± 0.11** | 0.24 ± 0.13** | 0.27 ± 0.14** | 0.23 ± 0.09* |
| control | — | 0.24 ± 0.17 | 0.44 ± 0.17 | 0.54 ± 0.06 | 0.37 ± 0.21 |

Results: The toes of the rats in each group were swollen rapidly after modeling. The swelling peak was reached at about 3~5 h and disappeared at 7 h. The mPEG$_2$-ALD-1 group with different molecular weights could significantly inhibit the rat toe swelling induced by carrageenan, and the high dose group was better than the low dose group, of which mPEG$_2$-ALD$_{10k}$-HM-1 at the dose of 40 mg/kg was most effective.

TABLE 46 mPEG-bALD-HM-1Effect on carrageenan-induced acute inflammation of rat toe swelling

| group | dose (mg/kg) | Swelling (mg) | | | |
|---|---|---|---|---|---|
| | | 1 h | 3 h | 5 h | 7 h |
| mPEG-bALD$_{5k}$-HM-1 | 10 | 0.23 ± 0.11 | 0.34 ± 0.12 | 0.40 ± 0.14 | 0.32 ± 0.11* |
| | 20 | 0.22 ± 0.13* | 0.33 ± 0.18 | 0.36 ± 0.15** | 0.34 ± 0.12* |
| mPEG-bALD$_{10k}$-HM-1 | 20 | 0.22 ± 0.14 | 0.32 ± 0.15 | 0.41 ± 0.17 | 0.31 ± 0.12* |
| | 40 | 0.20 ± 0.12* | 0.32 ± 0.22 | 0.38 ± 0.14** | 0.32 ± 0.11* |
| mPEG-bALD$_{20k}$-HM-1 | 40 | 0.25 ± 0.15* | 0.35 ± 0.14 | 0.42 ± 0.15* | 0.36 ± 0.18* |
| | 80 | 0.27 ± 0.11* | 0.34 ± 0.10 | 0.41 ± 0.12* | 0.33 ± 0.17* |
| mPEG-bALD$_{40k}$-HM-1 | 80 | 0.28 ± 0.15* | 0.33 ± 0.12 | 0.45 ± 0.16* | 0.37 ± 0.18* |
| | 160 | 0.25 ± 0.12* | 0.36 ± 0.13 | 0.46 ± 0.17* | 0.36 ± 0.19* |
| Dex | 10 | 0.21 ± 0.10** | 0.23 ± 0.12** | 0.28 ± 0.12** | 0.24 ± 0.10* |
| control | — | 0.23 ± 0.16 | 0.45 ± 0.16 | 0.55 ± 0.07 | 0.38 ± 0.20 |

Results: The toes of the rats in each group were swollen rapidly after modeling. The swelling peak was reached at about 3~5 h and disappeared at 7 h. The mPEG-bALD-HM-1 group with different molecular weights could significantly inhibit the rat toe swelling induced by carrageenan, and the high dose group was better than the low dose group, of which mPEG-bALD$_{10k}$-HM-1 at the dose of 40 mg/kg was most effective.

Example 12: Inhibitory Effect of mPEG-HM-1 on Proliferation of Human Retinal Vascular Endothelial Cells (HRCEC)

The activity of the angiogenesis inhibitor polypeptide to inhibit proliferation of human retinal vascular endothelial cells was examined by MTT assay. HRCEC cells were cultured in a 37° C., 5% CO$_2$ incubator to a density of 90% or more, and collected by trypsinization. The cells were resuspended in the culture medium and counted under a microscope to adjust the cell concentration to 3.0×10$^4$ cells/mL. The cell suspension was inoculated into a 96-well plate at 100 μL per well and cultured overnight at 37° C. in a 5% CO$_2$ incubator. After the cells were completely adhered, the angiogenesis inhibitor polypeptide was added as the administration group, and Avastin was used as the positive control group, and the culture media without any drug was used as a blank control group, and the culture media were diluted to each predetermined concentration. Each dilution was separately added to a 96-well plate at 100 μL per well and incubated for 48 h at 37° C. in a 5% CO$_2$ incubator. 20 μL of 5 mg/mL MTT was added to each well of a 96-well plate and incubation was continued for 4 h. The medium was aspirated and dissolved in 100 μL of DMSO per well. The absorbance was measured with a microplate reader at a detection wavelength of 570 nm and a reference wavelength of 630 nm, and the proliferation inhibition rate (PI) was calculated. The formula is as follows:

PI (%)=1−administration group/negative group

The test was repeated 3 times independently. The results obtained by the test were expressed as mean±SD, and a statistical T test was performed. *P<0.05 was a significant difference, and **P<0.01 was a very significant difference. The test results are shown in Table 47.

TABLE 47 mPEG-SC-HM-1 Inhibitory effect on proliferation of human retinal vascular endothelial cells (HRCEC)

| Group | Dose (μg/mL) | A570 nm-A630 nm | Inhibition rate (%) |
|---|---|---|---|
| mPEG-SC$_{5k}$-HM-1 | 20 | 0.7573 ± 0.09088 | 42.22%* |
| | 40 | 0.6323 ± 0.08797 | 51.76%** |
| | 60 | 0.4968 ± 0.08679 | 62.10%* |
| mPEG-SC$_{10k}$-HM-1 | 40 | 0.7020 ± 0.07964 | 46.44%* |
| | 60 | 0.5847 ± 0.07356 | 55.39%** |
| | 80 | 0.4084 ± 0.07298 | 68.84%* |
| mPEG-SC$_{20k}$-HM-1 | 60 | 0.7116 ± 0.07539 | 45.71%* |
| | 80 | 0.6040 ± 0.06996 | 53.92%** |
| | 100 | 0.4372 ± 0.07210 | 66.64%* |
| mPEG-SC$_{40k}$-HM-1 | 80 | 0.7567 ± 0.07109 | 42.27%* |
| | 100 | 0.6139 ± 0.07120 | 53.16%** |
| | 120 | 0.4760 ± 0.07009 | 63.68%* |
| Avastin control | 10 | 0.4479 ± 0.08104 | 65.83%** |
| | — | 1.3107 ± 0.09405 | 0.00% |

Results: mPEG-SC-HM-1 with different molecular weights could significantly inhibit the proliferation of HRCEC and showed a dose-dependent relationship. The inhibition rate of high-dose group was close to that of control Avastin, and mPEG-SC$_{10k}$-HM-1 at the dosage of 80 μg/mL reached an inhibition rate of 68.84%, which was slightly higher than that of the positive control Avastin.

TABLE 48 mPEG$_2$-NHS-HM-1 Inhibitory effect on proliferation of human retinal vascular endothelial cells (HRCEC)

| Group | Dose (μg/mL) | A570 nm-A630 nm | Inhibition rate (%) |
|---|---|---|---|
| mPEG$_2$-NHS$_{5k}$-HM-1 | 20 | 0.7807 ± 0.09103 | 40.94%* |
| | 40 | 0.6523 ± 0.08688 | 50.65%** |
| | 60 | 0.5144 ± 0.08531 | 61.08%* |
| mPEG$_2$-NHS$_{10k}$-HM-1 | 40 | 0.7160 ± 0.07829 | 45.83%* |
| | 60 | 0.5985 ± 0.07472 | 54.72%** |
| | 80 | 0.4609 ± 0.07165 | 65.13%* |
| mPEG$_2$-NHS$_{20k}$-HM-1 | 60 | 0.7401 ± 0.07482 | 44.01%* |
| | 80 | 0.6056 ± 0.07003 | 54.18%** |
| | 100 | 0.4677 ± 0.07601 | 64.62%* |
| mPEG$_2$-NHS$_{40k}$-HM-1 | 80 | 0.7598 ± 0.07143 | 42.52%* |
| | 100 | 0.6363 ± 0.07532 | 51.86%** |
| | 120 | 0.4920 ± 0.07953 | 62.78%* |
| Avastin control | 10 | 0.4636 ± 0.08322 | 64.93%** |
| | — | 1.3218 ± 0.08917 | 0.00% |

Results: mPEG$_2$-NHS-HM-1 with different molecular weights could significantly inhibit the proliferation of HRCEC and showed a dose-dependent relationship. The inhibition rate of high-dose group was close to that of control Avastin, and mPEG$_2$-NHS$_{10k}$-HM-1 at the dosage of 80 μg/mL reached an inhibition rate of 65.13%, which was slightly higher than that of the positive control Avastin.

TABLE 49 mPEG-ALD-HM-1 Inhibitory effect on proliferation of human retinal vascular endothelial cells (HRCEC)

| Group | Dose (μg/mL) | A570 nm-A630 nm | Inhibition rate (%) |
|---|---|---|---|
| mPEG-ALD$_{5k}$-HM-1 | 20 | 0.7599 ± 0.08933 | 42.02%* |
| | 40 | 0.6301 ± 0.08011 | 51.93%** |
| | 60 | 05042 ± 0.08135 | 61.53%* |
| mPEG-ALD$_{10k}$-HM-1 | 40 | 0.6771 ± 0.07904 | 48.34%* |
| | 60 | 0.5424 ± 0.07508 | 58.62%** |
| | 80 | 0.3422 ± 0.07412 | 73.89%* |
| mPEG-ALD$_{20k}$-HM-1 | 60 | 0.7050 ± 0.07965 | 46.21%* |
| | 80 | 0.5780 ± 0.06987 | 55.90%** |
| | 100 | 0.4175 ± 0.07301 | 68.15%* |
| mPEG-ALD$_{40k}$-HM-1 | 80 | 0.7457 ± 0.07094 | 43.11%* |
| | 100 | 0.5999 ± 0.07138 | 54.23%** |
| | 120 | 0.4970 ± 0.07653 | 62.08%* |
| Avastin control | 10 | 0.4494 ± 0.08132 | 65.71%** |
| | — | 1.3107 ± 0.09314 | 0.00% |

Results: mPEG-ALD-HM-1 with different molecular weights could significantly inhibit the proliferation of HRCEC and showed a dose-dependent relationship. The inhibition rate of high-dose group was close to that of control Avastin, mPEG-ALD$_{10k}$-HM-1 at the dosage of 80 μg/mL reached an inhibition rate of 73.89%, mPEG-ALD$_{20k}$-HM-1 at the dosage of 100 μg/mL reached an inhibition rate of 68.15%, which were higher than that of the positive control Avastin.

TABLE 50 mPEG-bALD-HM-1 Inhibitory effect on proliferation of human retinal vascular endothelial cells (HRCEC)

| Group | Dose (μg/mL) | A570 nm-A630 nm | Inhibition rate (%) |
|---|---|---|---|
| mPEG-bALD$_{5k}$-HM-1 | 20 | 0.7747 ± 0.08752 | 41.82%* |
| | 40 | 0.6594 ± 0.08003 | 50.48%** |
| | 60 | 04958 ± 0.07902 | 62.77%* |
| mPEG-bALD$_{10k}$-HM-1 | 40 | 0.6931 ± 0.07754 | 47.95%* |
| | 60 | 0.5669 ± 0.07609 | 57.43%** |
| | 80 | 0.3304 ± 0.07354 | 75.19%* |
| mPEG-bALD$_{20k}$-HM-1 | 60 | 0.6987 ± 0.07838 | 47.53%* |
| | 80 | 0.5683 ± 0.07055 | 57.32%** |
| | 100 | 0.4112 ± 0.07405 | 69.12%* |
| mPEG-bALD$_{40k}$-HM-1 | 80 | 0.7349 ± 0.07082 | 44.81%* |
| | 100 | 0.5988 ± 0.07291 | 55.03%** |
| | 120 | 0.4911 ± 0.07534 | 63.12%* |
| Avastin control | 10 | 0.4518 ± 0.08013 | 66.07%** |
| | — | 1.3316 ± 0.09051 | 0.00% |

Results: mPEG-bALD-HM-1 with different molecular weights could significantly inhibit the proliferation of HRCEC and showed a dose-dependent relationship. The inhibition rate of high-dose group was close to that of control Avastin, mPEG-bALD$_{10k}$-HM-1 at the dosage of 80 μg/mL reached an inhibition rate of 75.19%, mPEG-ALD$_{20k}$-HM-1 at the dosage of 100 μg/mL reached an inhibition rate of 69.12%, which were higher than that of the positive control Avastin.

Example 13: Effect of mPEG-HM-1 on Corneal Neovascularization in BALB/c Mice (1) Preparation of corneal neovascularization model induced by alkali burn in BALB/c mice: mice were randomly grouped and labeled as mPEG-HM-1 experimental group and control group, 5 rats in each group, respectively, was given mPEG-HM-1 and saline by Intravitreal injection after alkali burn, once a day for 1 week. The inflammatory reaction and neovascularization of the cornea were observed under slit lamp microscope at 1 d, 7 d, and 14 d after alkali burn. On the 14th day after alkali burn, the corneal neovascularization was recorded under the slit lamp microscope in the anterior segment of the eye. All the mice were euthanized by cervical dislocation and the eyeballs were removed, washed with saline to rid of blood, and was fixed in 4% paraformaldehyde for 1.5 h, dehydrated in PBS containing 30% sucrose overnight, embedded in OCT frozen section embedding agent, stored in −80° C. refrigerator, frozen section 8 μm, and underwent immunocytochemical detection of CD31 expression.

(2) Quantitative measurement of corneal tissue microvessel density: Microvessel density (MVD) is an indicator for evaluating angiogenesis. Vascular endothelial cells were labeled with anti-CD31 antibody by immunohistochemistry, and the number of microvessels per unit area was counted to measure the degree of neovascularization. Standards for counting microvessels: Microscopically, the endothelial cells or cell clusters that are clearly demarcated from adjacent tissues in the corneal tissue and stained brown or brown are counted in the neovascularization. The number of new blood vessels in the whole section was counted under a 10×20 microscope. After the corneal tissue was photographed, the entire corneal tissue area was calculated by image processing software Image J, and the neovascular density of the whole section was determined.

The test was repeated 3 times independently. The results obtained by the test were expressed as mean±SD, and a statistical T test was performed. *$P<0.05$ was a significant difference, and **$P<0.01$ was a very significant difference. The test results are shown in Table 51.

TABLE 51 mPEG-HM-1 Effect on corneal neovascularization in mice

| Group | MVD | Inhibition rate (%) |
|---|---|---|
| mPEG-SC$_{5k}$-HM-1 | 39.69 ± 3.527* | 40.52% |
| mPEG-SC$_{10k}$-HM-1 | 31.92 ± 3.648** | 52.17% |
| mPEG-SC$_{20k}$-HM-1 | 35.68 ± 4.842** | 46.53% |
| mPEG-SC$_{40k}$-HM-1 | 37.72 ± 4.153** | 43.48% |
| mPEG$_2$-NHS$_{5k}$-HM-1 | 39.95 ± 3.985* | 40.13% |
| mPEG$_2$-NHS$_{10k}$-HM-1 | 33.32 ± 3.871** | 50.07% |
| mPEG$_2$-NHS$_{20k}$-HM-1 | 38.46 ± 4.528** | 42.37% |
| mPEG$_2$-NHS$_{40k}$-HM-1 | 37.91 ± 4.273** | 43.19% |
| mPEG-ALD$_{5k}$-HM-1 | 36.64 ± 3.909* | 45.09% |
| mPEG-ALD$_{10k}$-HM-1 | 30.81 ± 5.465** | 53.83% |
| mPEG-ALD$_{20k}$-HM-1 | 34.67 ± 6.953** | 48.04% |
| mPEG-ALD$_{40k}$-HM-1 | 35.96 ± 6.862** | 46.11% |
| mPEG-bALD$_{5k}$-HM-1 | 37.97 ± 3.914* | 43.10% |
| mPEG-bALD$_{10k}$-HM-1 | 32.01 ± 5.738** | 52.03% |
| mPEG-bALD$_{20k}$-HM-1 | 34.81 ± 6.817** | 47.84% |
| mPEG-bALD$_{40k}$-HM-1 | 36.52 ± 6.537** | 45.27% |
| control | 66.73 ± 8.324 | 0.00% |

The results showed that mPEG-HM-1 with different molecular composition and different molecular weights could significantly inhibit the growth of corneal neovascularization, and the inhibition rate of mPEG-SC$_{10k}$-HM-1 reached 52.17%, and the inhibition rate of mPEG$_2$-NHS$_{10k}$-HM-1 reached 50.07%, the inhibition rate of mPEG-ALD$_{10k}$-HM-1 reached 53.83%, and the inhibition rate of mPEG-bALD$_{10k}$-HM-1 reached 52.03%.

Example 14: Effect of mPEG-HM-1 on Iris Neovascularization in Rabbits

The main branch vein of rabbit retina was condensed by 577 nm argon ion laser. The venous occlusion was confirmed by fundus fluorescein angiography (FFA). After 5-12 days, the iris fluorescein angiography (IFA) showed that the fluorescein leakage was obvious in the iris vessels compared with the normal control group, confirming the formation of the iris neovascularization animal model (NVI).

51 eyes with successful modeling were randomly divided into groups of 3 each. They were labeled as negative control group, mPEG-SC-HM-1 treatment group, mPEG$_2$-NHS-HM-1 treatment group, mPEG-ALD-HM-1 treatment group and mPEG-bALD-HM-1 treatment group, respectively. Saline, mPEG-HM-1 (see Table 52 for dosing) was administered intravitreally, once daily for 2 weeks. On the third week the eyes were observed by optical and electron microscopy.

TABLE 52 dose of mPEG-HM-1 treatment group

| Group | | Dose (μg) |
|---|---|---|
| mPEG-SC-HM-1 treatment group | mPEG-SC$_{5k}$-HM-1 | 25 |
| | mPEG-SC$_{10k}$-HM-1 | 50 |
| | mPEG-SC$_{20k}$-HM-1 | 100 |
| | mPEG-SC$_{40k}$-HM-1 | 200 |
| mPEG$_2$-NHS-HM-1 treatment group | mPEG$_2$-NHS$_{5k}$-HM-1 | 25 |
| | mPEG$_2$-NHS$_{10k}$-HM-1 | 50 |
| | mPEG$_2$-NHS$_{20k}$-HM-1 | 100 |
| | mPEG$_2$-NHS$_{40k}$-HM-1 | 200 |
| mPEG-ALD-HM-1 treatment group | mPEG-ALD$_{5k}$-HM-1 | 25 |
| | mPEG-ALD$_{10k}$-HM-1 | 50 |
| | mPEG-ALD$_{20k}$-HM-1 | 100 |
| | mPEG-ALD$_{40k}$-HM-1 | 200 |
| mPEG-bALD-HM-1 treatment group | mPEG-bALD$_{5k}$-HM-1 | 25 |
| | mPEG-bALD$_{10k}$-HM-1 | 50 |
| | mPEG-bALD$_{20k}$-HM-1 | 100 |
| | mPEG-bALD$_{40k}$-HM-1 | 200 |

Results: Under the optical microscope, it was observed that the anterior surface of the iris was mainly composed of fibrous vascular membrane residue composed of fibrous tissue, and there were few open vascular lumens. Vascular remnants can be seen in the iris matrix, which are necrotic cells and cell debris. In the iris surface of the control eye, under light microscope, fibrous vascular membrane with branch and potential lumen can be observed; the ultrastructure of the iris in the treatment group has a series of degenerative changes: the endothelial cells of the large blood vessels in the center of the iris matrix have normal nucleus, cytoplasm and cell junctions, capillary remnants were found in the iris matrix and on the anterior surface of the iris, surrounded by cell debris and macrophage infiltration, no potential lumen capillaries and degenerated wall cells, indicating neovascularization subsided.

The results showed that mPEG-HM-1 can inhibit the formation of iris neovascularization in rabbits and cause the formed blood vessels to degenerate.

Example 15: Effect of mPEG-HM-1 on Choroidal Neovascularization in Rats 6-8 weeks old male BN rats were anesthetized with 846 compound anesthetic 0.5 mL/kg administered intraperitoneally. The eye drops of compound tropamide eyes were used 5 minutes before laser photocoagulation, and the pupils of both eyes were fully scattered. Fix animals, with the aid of −53.00 D contact lens, around the optic disc and along the same distance from the optic disc 2PD, the laser beam photocoagulation were performed to make a total of 8 photo-condensation spots, with laser wavelength of 647.1 nm, power of 350 mW, photocoagulation spot diameter and time were 50 μm and 0.05 s, respectively. Immediately after photocoagulation, fundus photography was performed. FFA, histopathology and transmission electron microscopy were performed at 3, 7, 14, 21, and 28 days after photocoagulation.

It was confirmed by fundus photography and FFA examination that the fluorescein leakage of photocoagulation peaked on the 21st day after photocoagulation, and histopathological examination was performed at the same time. After 21 days of photocoagulation, CNV showed significant fibrovascular proliferation under light microscopy. A large number of neovascular vessels were seen, and red blood cells were visible in the lumen. Microscopically, capillary cells in the choroidal melanocytes were cohesively altered and endothelial cells aggregated. These showed that a rat choroidal neovascular model was formed 21 days later.

Rats that were successfully modeled were randomly divided into groups of 5 rats each. They were labeled as negative control group, mPEG-SC-HM-1 treatment group, mPEG$_2$-NHS-HM-1 treatment group, mPEG-ALD-HM-1 treatment group and mPEG-bALD-HM-1 treatment group, respectively. Saline, mPEG-HM-1 (see Table 53 for dosing) was administered intravitreally, once daily for 1 week. FFA examinations were performed 3 days, 7 days, 14 days, and 28 days after administration of the modified peptides. The test results are shown in Tables 54 to 57.

TABLE 53

Dosage of mPEG-HM-1 treatment group

| group | | dose (μg) |
|---|---|---|
| mPEG-SC-HM-1 treatment group | mPEG-SC$_{5k}$-HM-1 | 25 |
| | mPEG-SC$_{10k}$-HM-1 | 50 |
| | mPEG-SC$_{20k}$-HM-1 | 100 |
| | mPEG-SC$_{40k}$-HM-1 | 200 |
| mPEG$_2$-NHS-HM-1 treatment group | mPEG$_2$-NHS$_{5k}$-HM-1 | 25 |
| | mPEG$_2$-NHS$_{10k}$-HM-1 | 50 |
| | mPEG$_2$-NHS$_{20k}$-HM-1 | 100 |
| | mPEG$_2$-NHS$_{40k}$-HM-1 | 200 |
| mPEG-ALD-HM-1 treatment group | mPEG-ALD$_{5k}$-HM-1 | 25 |
| | mPEG-ALD$_{10k}$-HM-1 | 50 |
| | mPEG-ALD$_{20k}$-HM-1 | 100 |
| | mPEG-ALD$_{40k}$-HM-1 | 200 |
| mPEG-bALD-HM-1 treatment group | mPEG-bALD$_{5k}$-HM-1 | 25 |
| | mPEG-bALD$_{10k}$-HM-1 | 50 |
| | mPEG-bALD$_{20k}$-HM-1 | 100 |
| | mPEG-bALD$_{40k}$-HM-1 | 200 |

TABLE 54 mPEG-SC-HM-1 Effect on choroidal neovascularization in rats

| | Test time | | | | | | | |
|---|---|---|---|---|---|---|---|---|
| | Day 3 The total number of spots is 296 | | Day 7 The total number of spots is 188 | | Day 14 The total number of spots is 135 | | Day 28 The total number of spots is 67 | |
| group | leakage Spots # | CNV Incidence rate (%) | leakage Spots # | CNV Incidence rate (%) | leakage Spots # | CNV Incidence rate (%) | leakage Spots # | CNV Incidence rate (%) |
| control | 246 | 83.11% | 142 | 75.53% | 89 | 65.93% | 40 | 59.70% |
| mPEG-SC$_{5k}$-HM-1 | 162 | 54.73% | 100 | 53.19% | 65 | 48.15% | 32 | 47.76% |
| mPEG-SC$_{10k}$-HM-1 | 147 | 49.66% | 86 | 45.74% | 58 | 42.96% | 26 | 38.81% |
| mPEG-SC$_{20k}$-HM-1 | 152 | 51.35% | 92 | 48.94% | 62 | 45.93% | 28 | 41.79% |
| mPEG-SC$_{40k}$-HM-1 | 150 | 50.68% | 94 | 50.00% | 60 | 44.44% | 29 | 43.28% |

Results: FFA detection, 3 days after administration, the fluorescein leakage in the mPEG-SC-HM-1 treatment group was significantly different from that before administration; the fluorescein leakage in the treatment group was gradually reduced 7 and 14 days after administration of the peptides compared to before administration; fluorescein leakage was even less on 28 days after administration compared to 14 days after administration. The results indicated that mPEG-SC-HM-1 could treat choroidal neovascularization in rats. The effect of mPEG-SC$_{10k}$-HM-1 was the most obvious. The incidence of CNV was the lowest at 38.81% 28 days after administration.

TABLE 55 mPEG$_2$-NHS-HM-1 Effect on choroidal neovascularization in rats

| | Test time | | | | | | | |
|---|---|---|---|---|---|---|---|---|
| | Day 3 The total number of spots is 294 | | Day 7 The total number of spots is 182 | | Day 14 The total number of spots is 137 | | Day 28 The total number of spots is 68 | |
| group | leakage Spots # | CNV Incidence rate (%) | leakage Spots # | CNV Incidence rate (%) | leakage Spots # | CNV Incidence rate (%) | leakage Spots # | CNV Incidence rate (%) |
| control | 249 | 84.69% | 144 | 79.12% | 88 | 64.23% | 42 | 61.76% |
| mPEG$_2$-NHS$_{5k}$-HM-1 | 165 | 56.12% | 101 | 55.49% | 63 | 45.99% | 33 | 48.53% |

TABLE 55-continued mPEG₂-NHS-HM-1 Effect on choroidal neovascularization in rats

| | Test time | | | | | | | |
|---|---|---|---|---|---|---|---|---|
| | Day 3 The total number of spots is 294 | | Day 7 The total number of spots is 182 | | Day 14 The total number of spots is 137 | | Day 28 The total number of spots is 68 | |
| group | leakage Spots # | CNV Incidence rate (%) | leakage Spots # | CNV Incidence rate (%) | leakage Spots # | CNV Incidence rate (%) | leakage Spots # | CNV Incidence rate (%) |
| mPEG₂-NHS₁₀ₖ-HM-1 | 148 | 50.34% | 88 | 48.35% | 59 | 43.07% | 27 | 39.71% |
| mPEG₂-NHS₂₀ₖ-HM-1 | 155 | 52.72% | 95 | 52.20% | 63 | 45.99% | 29 | 42.65% |
| mPEG₂-NHS₄₀ₖ-HM-1 | 150 | 51.02% | 93 | 51.10% | 61 | 44.53% | 28 | 41.18% |

Results: FFA detection, 3 days after administration, the fluorescein leakage in the mPEG₂-NHS-HM-1 treatment group was significantly different from that before administration; the fluorescein leakage in the treatment group was gradually reduced 7 and 14 days after administration of the peptides compared to before administration; fluorescein leakage was even less on 28 days after administration compared to 14 days after administration. The results indicated that mPEG₂-NHS-HM-1 could treat choroidal neovascularization in rats. The effect of mPEG₂-NHS₁₀ₖ-HM-1 was the most obvious. The incidence of CNV was the lowest at 39.71% 28 days after administration.

TABLE 56 mPEG-ALD-HM-1 Effect on choroidal neovascularization in rats

| | Test time | | | | | | | |
|---|---|---|---|---|---|---|---|---|
| | Day 3 The total number of spots is 290 | | Day 7 The total number of spots is 182 | | Day 14 The total number of spots is 132 | | Day 28 The total number of spots is 71 | |
| group | leakage Spots # | CNV Incidence rate (%) | leakage Spots # | CNV Incidence rate (%) | leakage Spots # | CNV Incidence rate (%) | leakage Spots # | CNV Incidence rate (%) |
| control | 242 | 83.45% | 140 | 76.92% | 87 | 65.91% | 42 | 59.15% |
| mPEG-ALD₅ₖ-HM-1 | 160 | 55.17% | 96 | 52.75% | 62 | 46.97% | 33 | 46.48% |
| mPEG-ALD₁₀ₖ-HM-1 | 141 | 48.62% | 84 | 46.15% | 55 | 41.67% | 28 | 39.44% |
| mPEG-ALD₂₀ₖ-HM-1 | 150 | 51.72% | 89 | 48.90% | 60 | 45.45% | 29 | 40.85% |
| mPEG-ALD₄₀ₖ-HM-1 | 152 | 52.41% | 92 | 50.55% | 62 | 46.97% | 30 | 42.25% |

Results: FFA detection, 3 days after administration, the fluorescein leakage in the mPEG-ALD-HM-1 treatment group was significantly different from that before administration; the fluorescein leakage in the treatment group was gradually reduced 7 and 14 days after administration of the peptides compared to before administration; fluorescein leakage was even less on 28 days after administration compared to 14 days after administration. The results indicated that mPEG-ALD-HM-1 could treat choroidal neovascularization in rats. The effect of mPEG-ALD₁₀ₖ-HM-1 was the most obvious. The incidence of CNV was the lowest at 39.44% 28 days after administration.

TABLE 57 mPEG-bALD-HM-1 Effect on choroidal neovascularization in rats

| | Test time | | | | | | | |
|---|---|---|---|---|---|---|---|---|
| | Day 3 The total number of spots is 293 | | Day 7 The total number of spots is 185 | | Day 14 The total number of spots is 138 | | Day 28 The total number of spots is 69 | |
| group | leakage Spots # | CNV Incidence rate (%) | leakage Spots # | CNV Incidence rate (%) | leakage Spots # | CNV Incidence rate (%) | leakage Spots # | CNV Incidence rate (%) |
| control | 243 | 82.94% | 142 | 76.76% | 90 | 65.22% | 41 | 59.42% |
| mPEG-bALD₅ₖ-HM-1 | 162 | 55.29% | 97 | 52.43% | 65 | 47.10% | 32 | 46.38% |
| mPEG-bALD₁₀ₖ-HM-1 | 142 | 48.46% | 86 | 46.49% | 58 | 42.03% | 27 | 39.13% |
| mPEG-bALD₂₀ₖ-HM-1 | 151 | 51.54% | 91 | 49.19% | 63 | 45.65% | 28 | 40.58% |
| mPEG-bALD₄₀ₖ-HM-1 | 153 | 52.22% | 94 | 50.81% | 65 | 47.10% | 29 | 42.03% |

Results: FFA detection, 3 days after administration, the fluorescein leakage in the mPEG-bALD-HM-1 treatment group was significantly different from that before administration; the fluorescein leakage in the treatment group was gradually reduced 7 and 14 days after administration of the peptides compared to before administration; fluorescein leakage was even less on 28 days after administration compared to 14 days after administration. The results indicated that mPEG-bALD-HM-1 could treat choroidal neovascularization in rats. The effect of mPEG-ALD$_{10k}$-HM-1 was the most obvious. The incidence of CNV was the lowest at 39.13% 28 days after administration.

Example 16: Effect of mPEG-HM-1 on Retinal Blood Vessels in OIR Mice

Establishment of the OIR model: Exposure of young mouse and their mothers to 75% hyperoxic environment from day 7 to day 12 after birth of C57/B16 mice caused rapid disappearance of capillaries in the central retina. Upon returning to the indoor air on the 12th day, the retinal blood vessels, upon exposing to hyperoxia, rapidly disappeared, causing extensive abnormal neovascularization, and the central portion of the retina remained largely avascular for a long time. After the blood vessels disappeared completely, on the 13th day, physiological saline (negative control group), mPEG-SC-HM-1, mPEG$_2$-NHS-HM-1, mPEG-ALD$_{10k}$-HM-1, and mPEG-bALD-HM-1, were administered by intravitreal injection and retinal vessels were evaluated on day 17 (to label unclosed vessels, 50 mL of Texas Red-labeled tomato lectin was injected into the left ventricle and circulated for 5 min). The test results are shown in Table 58.

TABLE 58 mPEG-HM-1 Effect on retinal blood vessels in OIR mice

| Group | doses (µg) | Neovascular clusters area (mm$^2$) | Inhibition rate (%) |
| --- | --- | --- | --- |
| control | — | 0.221 ± 0.006 | 0.00% |
| mPEG-SC$_{5k}$-HM-1 | 25 | 0.116 ± 0.012 | 47.42%* |
| mPEG-SC$_{10k}$-HM-1 | 50 | 0.096 ± 0.008 | 56.56%** |
| mPEG-SC$_{20k}$-HM-1 | 100 | 0.110 ± 0.010 | 50.23%** |
| mPEG-SC$_{40k}$-HM-1 | 200 | 0.119 ± 0.005 | 46.18%* |
| mPEG$_2$-NHS$_{5k}$-HM-1 | 25 | 0.119 ± 0.007 | 46.35%* |
| mPEG$_2$-NHS$_{10k}$-HM-1 | 50 | 0.100 ± 0.006 | 54.63%** |
| mPEG$_2$-NHS$_{20k}$-HM-1 | 100 | 0.112 ± 0.011 | 49.27%** |
| mPEG$_2$-NHS$_{40k}$-HM-1 | 200 | 0.120 ± 0.008 | 45.92%** |
| mPEG-ALD$_{5k}$-HM-1 | 25 | 0.108 ± 0.006 | 50.98%** |
| mPEG-ALD$_{10k}$-HM-1 | 50 | 0.085 ± 0.007 | 61.75%** |
| mPEG-ALD$_{20k}$-HM-1 | 100 | 0.095 ± 0.009 | 57.03%** |
| mPEG-ALD$_{40k}$-HM-1 | 200 | 0.106 ± 0.010 | 52.02%** |
| mPEG-bALD$_{5k}$-HM-1 | 25 | 0.108 ± 0.008 | 51.17%** |
| mPEG-bALD$_{10k}$-HM-1 | 50 | 0.083 ± 0.006 | 62.35%** |
| mPEG-bALD$_{20k}$-HM-1 | 100 | 0.097 ± 0.011 | 56.22%** |
| mPEG-bALD$_{40k}$-HM-1 | 200 | 0.110 ± 0.012 | 50.31%** |

Compared with the negative control, the neovascular clusters in the retina of OIR mice treated with mPEG-SC-HM-1, mPEG$_2$-NHS-HM-1, mPEG-ALD$_{10k}$-HM-1, and mPEG-bALD-HM-1 were significantly reduced. Among them, mPEG-SC$_{10k}$-HM-1 was the best in the mPEG-SC-HM-1 administration group, and the inhibition rate was 56.56% when the dosage was 50 µg. Among the mPEG$_2$-NHS-HM-1 administration group, the most effective is mPEG$_2$-NHS$_{10k}$-HM-1, wherein the inhibition rate is 54.63% when the dosage is 50 µg; mPEG-ALD$_{10k}$-HM-1 is the best among the mPEG-ALD-HM-1 administration group. The inhibition rate reached 61.75% at 50 µg; mPEG-bALD$_{10k}$-HM-1 is the best in the mPEG-bALD-HM-1 administration group, and the inhibition rate reached 62.35% when the dose was 50 µg.

Example 17: Effect of mPEG-HM-1 on Neovascularization in Rat Models of Premature Retinopathy A fluctuating oxygen-induced animal model was used to randomly divide the newborn rats that were naturally delivered on the same day (within 12 hours) into three groups: the oxygenated model group, the oxygenated treatment group, and the normal control group. The oxygenated model group was subdivided into three subgroup models and along with the oxygenated treatment group was placed in a semi-closed oxygen chamber made of plexiglass. The chamber was connected to medical oxygen, and the oxygen analyzer was adjusted to a concentration of 80%±2%. After 24 hours, Nitrogen gas was introduced into the oxygen chamber, and the oxygen concentration was adjusted to 10%±2% and maintained for 24 h. This process was repeated, so that the oxygen concentration in the oxygen chamber is switched between 80% and 10% every 24 hours, and then transferred to the air for 7 days. The oxygen concentration was monitored 8 times a day, and the ambient temperature in the control cabin was 23° C.±2° C. Bedding change, adding food, changing water and replacing mother rats were performed once a day. The normal control group was placed in an animal facility environment. Compared with the control group, modeling was considered successful if the ADP enzyme staining of the retinal patch showed obvious vascular changes, the number of vascular endothelial cells that broke through the inner retinal membrane into the vitreous was increased, and the difference was statistically significant.

The oxygenated therapeutic components were divided into four subgroups, and on the 7th day of modeling, mPEG-SC-HM-1, mPEG$_2$-NHS-HM-1, mPEG-ALD$_{10k}$-HM-1, and mPEG-bALD-HM-1 were respectively administered by intravitreal injection. Only normal saline was administered to the oxygen model group and the control group. The administrations continued for 1 week. On the 14th day, after being euthanized by ether anesthesia, eyeballs were removed, fixed in 40 g/L paraformaldehyde solution for 24 hours, dehydrated by gradient alcohol, and decolorized by xylene. After immersion in wax, serial section at thickness of 4 µm was performed, wherein the sections were kept away from the optic disc. The sections are parallel to the sagittal plane of the cornea to the optic disc. Ten sections per eyeball were randomly selected from each eyeball to be stained with hematoxylin and eosin, and the number of vascular endothelial cells that broke through the retinal inner membrane was counted (only the vascular endothelial nucleus closely related to the inner retinal membrane was counted), and the average numbers of endothelial cells per eyeball per slice was counted.

Results: in the control group, none or very few slices were found wherein vascular endothelial nuclei had broken through the inner retinal membrane into the vitreous body. In the model group, there were many vascular endothelial nuclei that had broken through the inner retinal membrane, some of which were isolated and some of which were clustered. At the same time, these vascular endothelial nuclei were also seen in some sections adjacent to the deep retina vessels, confirming that they originated from the retina instead of vitreous or other tissues of the eye. Only a few of the vascular endothelial nuclei that broke through the retinal membrane were observed in the sections of the treatment group. The experimental results are shown in table 59.

TABLE 59

Retinal vascular endothelial cell nuclei count

| Group | Dose (μg) | Cell nuclei count |
|---|---|---|
| mPEG-SC$_{5k}$-HM-1 | 25 | 9.104 ± 3.087 |
| mPEG-SC$_{10k}$-HM-1 | 50 | 8.528 ± 3.109 |
| mPEG-SC$_{20k}$-HM-1 | 100 | 7.372 ± 2.078 |
| mPEG-SC$_{40k}$-HM-1 | 200 | 8.089 ± 2.935 |
| mPEG$_2$-NHS$_{5k}$-HM-1 | 25 | 9.212 ± 3.134 |
| mPEG$_2$-NHS$_{10k}$-HM-1 | 50 | 8.786 ± 3.072 |
| mPEG$_2$-NHS$_{20k}$-HM-1 | 100 | 7.683 ± 2.914 |
| mPEG$_2$-NHS$_{40k}$-HM-1 | 200 | 8.495 ± 3.036 |
| mPEG-ALD$_{5k}$-HM-1 | 25 | 8.927 ± 2.902 |
| mPEG-ALD$_{10k}$-HM-1 | 50 | 7.581 ± 1.903 |
| mPEG-ALD$_{20k}$-HM-1 | 100 | 7.036 ± 1.315 |
| mPEG-ALD$_{40k}$-HM-1 | 200 | 8.673 ± 2.756 |
| mPEG-bALD$_{5k}$-HM-1 | 25 | 8.852 ± 2.933 |

TABLE 59-continued

Retinal vascular endothelial cell nuclei count

| Group | Dose (μg) | Cell nuclei count |
|---|---|---|
| mPEG-bALD$_{10k}$-HM-1 | 50 | 7.627 ± 1.892 |
| mPEG-bALD$_{20k}$-HM-1 | 100 | 7.158 ± 1.724 |
| mPEG-bALD$_{40k}$-HM-1 | 200 | 8.539 ± 2.218 |
| Model Group | — | 26.397 ± 2.104 |
| control | — | 1.317 ± 0.262 |

The results showed that compared to those in the oxygenated model group (26.397±2.104), the mPEG-HM-1 treatment groups had significantly lower nuclei counts of vascular endothelial cells, which proved that mPEG-HM-1 can inhibit the neovascularization of oxygen-induced retinopathy model in neonatal rats to certain extent. The best effect was generated by mPEG-ALD$_{20k}$-HM-1, and the cell count was 7.036±1.315 when the dose was 100 μg.

What is claimed is:

1. A polyethylene glycol-modified angiogenesis inhibitor HM-1, comprising the sequence of mPEG-Arg-Gly-Ala-Asp-Arg-Ala-Gly-Gly-Gly-Gly-Arg-Gly-Asp (SEQ ID NO: 1), wherein the mPEG is mPEG-ALD, with molecular weight ranging from 500 to 40,000 Dalton.

2. The polyethylene glycol-modified angiogenesis inhibitor HM-1 according to claim 1, comprising the following sequence:
   mPEG-ALD20k-Arg-Gly-Ala-Asp-Arg-Ala-Gly-Gly-Gly-Gly-Arg-Gly-Asp (SEQ ID NO: 1).

3. A medicament for treating tumors, comprising the polyethylene glycol-modified angiogenesis inhibitor HM-1 from claim 2.

4. The medicament of claim 3, wherein the tumors comprise a primary or secondary cancer, melanoma, hemangiomas, and sarcomas originating from human head, neck, brain, thyroid, esophagus, pancreas, lung, liver, stomach, breast, kidney, gallbladder, colon or rectum, ovary, cervix, uterus, prostate, bladder, and testis.

5. A medicament for treating tumors, comprising the polyethylene glycol-modified angiogenesis inhibitor HM-1 from claim 1.

6. The medicament of claim 5, wherein the tumors comprise a primary or secondary cancer, melanoma, hemangiomas, and sarcomas originating from human head, neck, brain, thyroid, esophagus, pancreas, lung, liver, stomach, breast, kidney, gallbladder, colon or rectum, ovary, cervix, uterus, prostate, bladder, and testis.

* * * * *